US008530477B2

(12) United States Patent
Braun et al.

(10) Patent No.: US 8,530,477 B2
(45) Date of Patent: Sep. 10, 2013

(54) TROPANE UREA DERIVATIVES, PREPARATION THEREOF AND THERAPEUTIC APPLICATION THEREOF AS MODULATORS OF THE ACTIVITY OF 11BETAHSD1

(75) Inventors: Alain Jean Braun, Paris (FR); Olivier Crespin, Paris (FR); Eric Nicolai, Paris (FR); Cecile Pascal, Paris (FR); Olivier Venier, Paris (FR)

(73) Assignee: Sanofi, Paris (FR)

( * ) Notice: Subject to any disclaimer, the term of this patent is extended or adjusted under 35 U.S.C. 154(b) by 112 days.

(21) Appl. No.: 13/126,195

(22) PCT Filed: Oct. 27, 2009

(86) PCT No.: PCT/FR2009/052060
§ 371 (c)(1),
(2), (4) Date: Aug. 22, 2011

(87) PCT Pub. No.: WO2010/049635
PCT Pub. Date: May 6, 2010

(65) Prior Publication Data
US 2011/0294809 A1 Dec. 1, 2011

(30) Foreign Application Priority Data
Oct. 28, 2008 (FR) ...................... 08 05974

(51) Int. Cl.
*A61K 31/497* (2006.01)
*C07D 401/14* (2006.01)

(52) U.S. Cl.
USPC ..................... 514/253.04; 544/362

(58) Field of Classification Search
USPC ..................... 544/362; 514/253.04
See application file for complete search history.

(56) References Cited

U.S. PATENT DOCUMENTS
2005/0065178 A1   3/2005   Basha et al.

FOREIGN PATENT DOCUMENTS
| FR | 2 902 791 A1 | 12/2007 |
|---|---|---|
| GB | 1 164 555 A | 9/1969 |
| WO | WO2005/028477 A1 | 3/2005 |
| WO | WO 2005/108368 | 11/2005 |
| WO | WO 2006/045716 A1 | 5/2006 |
| WO | WO 2007/063071 | 6/2007 |
| WO | WO 2009/067579 A1 | 5/2009 |

OTHER PUBLICATIONS

Andrews, Robert C. et al., "Effects of the 11Beta-Hydroxysteroid Dehydrogenase Inhibitor Carbenoxolone on Insulin Sensitivity in Men with Type 2 Diabetes," The Journal of Clinical Endocrinology & Metabolism (2003), vol. 88, pp. 285-291.

Barf, Tjeerd et al., "Arylsulfonamidothiazoles as a New Class of Potential Antidiabetic Drugs. Discovery of Potent and Selective Inhibitors of the 11Beta-Hydroxysteroid Dehydrogenase Type 1," Journal of Medicinal Chemistry (2002), vol. 45, No. 18, pp. 3813-3815.
Cooper, M. S. et al., "Expression and Functional Consequences of 11Beta-Hydroxysteroid Dehydrogenase Activity in Human Bone," Bone (2000), vol. 27, No. 3, pp. 375-381.
Davani, Behrous et al., "Type 1 11Beta-Hydoxysteroid Dehydrogenase Mediates Glucocorticoid Activation and Insulin Release in Pancreatic Islets," The Jounal of Biological Chemistry (2000), vol. 275, No. 45, pp. 34841-34844.
Hermanowski-Vosatka, Anne et al., "11Beta-HSD1 inhibition ameliorates metabolic syndrome and prevents progession of atherosclerosis in mice," The Jounal of Experimental Medicine (2005), vol. 202, No. 4, pp. 517-527.
Kotelevtsev, Yuri et al., "11Beta-Hydroxysteroid dehydrogenase type 1 knockout mice show attenuated glucocorticoid-inducible responses and resist hyperglycemia on obesity or stress," Proceedings from the National Academy of Sciences (1997), vol. 94, pp. 14924-14929.
Krunic, Aleksej et al., "Synthesis and monoamine transporter affinity of 3-aryl substituted trop-2-enes," Bioorganic & Medicinal Chemistry Letters (2005), vol. 15, pp. 5488-5493.
Lupien, Sonia J. et al., "Cortisol levels during human aging predict hippocampal atrophy and memory deficits," Nature Neuroscience (1998), vol. 1, No. 1, pp. 69-73.
Masuzaki, Hiroaki et al., "Transgenic amplification of glucocorticoid action in adipose tissue causes high blood pressure in mice," The Journal of Clinical Investigation (2003), vol. 112, No. 1, pp. 83-90.
Masuzaki, Hiroaki et al., "A Transgenic Model of Visceral Obesity and the Metabolic Syndrome," Science (2001), vol. 294, pp. 2166-2170.
Moisan, Marie-Pierre et al., "11Beta-Hydroxysteroid Dehydrogenase Bioactivity and Messenger RNA Expression in Rat Forebrain: Localization in Hypothalamus, Hippocampus, and Cortex," Endocrinology (1990), vol. 127, No. 3, pp. 1450-1455.
McEwen, Bruce S. et al., "Stress and cognitive function," Current Opinion in Neurobiology (1995), vol. 5, pp. 205-216.
Morton, Nicholas M. et al., "Improved Lipid and Lipoprotein Profile, Hepatic Insulin Sensitivity, and Glucose Tolerance in 11Beta-Hydroxysteroid Dehydrogenase Type 1 Null Mice," The Journal of Biological Chemistry (2001), vol. 276, No. 44, pp. 41293-41300.
Rauz, Saaeha et al., "Expression and Putative Role of 11Beta-Hydroxysteroid Dehydrogenase Isozymes within the Human Eye," Investigative Ophthalmology & Visual Science (2001), vol. 42, No. 9, pp. 2037-2042.
Reaven, Gerald M. et al., "Role of Insulin Resistance in Human Disease (Syndrome X): an Expanded Definition," Annual Review of Medicine (1993), vol. 44, pp. 121-131.
Sandeep, Thekkepat C. et al., "11Beta-Hydoxysteroid dehydrogenase inhibition improves cognitive function in healthy elderly men and type 2 diabetics," PNAS (2004), vol. 101, No. 17, pp. 6734-6739.
Stokes, John et al., "Distribution of Glucocorticoid and Mineralocorticoid Receptors and 11Beta-Hydroxysteroid Dehydrogenases in Human and Rat Ocular Tissues," Investigative Ophthalmology & Visual Science (2000), vol. 41, No. 7, pp. 1629-1638.

(Continued)

*Primary Examiner* — Rebecca Anderson
(74) *Attorney, Agent, or Firm* — Scully, Scott, Murphy & Presser P.C.

(57) ABSTRACT

The invention relates to tropane urea derivatives of general formula (I) and to the application thereof as modulators of the activity of 11β-hydroxysteroid dehydrogenose type 1 (11βHSD1).

9 Claims, No Drawings

(56) References Cited

OTHER PUBLICATIONS

Tomlinson, Jeremy W. et al., "11Beta-Hydroxysteroid Dehydrogenase Type 1: A Tissue-Specific Regulator of Glucocorticoid Response," Endocrine Reviews (2004), vol. 25, pp. 831-366.

Wajchenberg, Bernardo Leo et al., "Subcutaneous and Visceral Adipose Tissue: Their Relation to the Metabolic Syndrome," Endocrine Reviews (2000), vol. 21, pp. 697-738.

Wang, S. J. Y. et al., "Inhibiton of 11Beta-hydroxysteroid dehydogenase type 1 reduces food intake and weight gain but maintains energy expenditure in diet-induced obese mice," Diabetologia (2006), vol. 49, pp. 1333-1337.

Yau, Joyce L. W. et al., "Lack of tissue glucocorticoid reactivation in 11Beta-hydroxysteroid dehydrogenase type 1 knockout mice ameliorates age-related learning impairments," PNAS (2001), vol. 98, No. 8, pp. 4716-4721.

Krunic, Aleksej et al., "Synthesis and monoamine transporter affinity of 3-aryl substituted trop-2-enes," Bioorganic and Medicinal Chemistry Letters (2005), vol. 15, pp. 5488-5493.

International Search Report dated Mar. 3, 2010.

TROPANE UREA DERIVATIVES, PREPARATION THEREOF AND THERAPEUTIC APPLICATION THEREOF AS MODULATORS OF THE ACTIVITY OF 11BETAHSD1

The present invention relates to tropane urea derivatives, to the preparation thereof and to the therapeutic use thereof. The present compounds modulate the activity of 11β-hydroxysteroid dehydrogenase type 1 (11βHSD1) and are of use in the treatment of pathological conditions in which such a modulation is beneficial, as in the case of metabolic syndrome or non-insulin-dependent type 2 diabetes.

11β-Hydroxysteroid dehydrogenase type 1 (11βHSD1) locally catalyses the conversion of inactive glucocorticoids (cortisone in humans) to active glucocorticoids (cortisol in humans) in various tissues and organs, mainly the liver and the adipose tissue, but also in the muscles, bones, pancreas, endothelium and ocular tissue and in certain parts of the central nervous system. 11βHSD1 acts as a regulator of the action of glucocorticoids in the tissues and organs where it is expressed (Tomlinson et al., *Endocrine Reviews* 25(5), 831-866 (2004), Davani et al., *J. Biol. Chem.* 275, 34841 (2000); Moisan et al., *Endocrinology,* 127, 1450 (1990)).

The most important pathological conditions in which glucocorticoids and the inhibition of 11βHSD1 are involved are indicated hereinafter.

A. Obesity, Type 2 Diabetes and Metabolic Syndrome

The role of 11βHSD1 in obesity, type 2 diabetes and metabolic syndrome (also known as syndrome X or insulin resistance syndrome) where the symptoms include visceral obesity, glucose intolerance, insulin resistance, hypertension, type 2 diabetes and hyperlipidemia (*Reaven Ann. Rev Med* 44, 121 (1993)) is described in many publications. In humans, treatment with carbenoxolone (a nonspecific inhibitor of 11βHSD1) improves insulin sensitivity in slim volunteer patients and in type 2 diabetics (Andrews et al., *J. Clin. Endocrinol, Metab.* 88, 285 (2003)). Furthermore, mice in which the 11βHSD1 gene has been knocked out are resistant to hyperglycemia induced by stress and obesity, show attenuated induction of liver neoglucoaenesis enzymes (PEPCK and G6P) and exhibit an increased sensitivity to insulin in adipose tissue (Koteleystev et al., *Proc. Nat. Acad. Sci.* 94, 14924 (1997); Morton et al., *J. Biol. Chem.* 276, 41293 (2001)). Moreover, transgenic mice in which the 11βHSD1 gene has been overexpressed in adipose tissues exhibit a phenotype similar to that of human metabolic syndrome (Masuzaki et al., *Science* 294, 2166 (2001)). It should be noted that the phenotype observed exists without any increase in total circulating glucocorticoids, but is induced by the specific increase in active glucocorticoids in adipose deposits.

Moreover, new classes of specific 11βHSD1 inhibitors have recently emerged:

arylsulfonamidothiazoles have shown that they improve sensitivity to insulin and reduce the blood glucose level in mice exhibiting hyperglycemia (Barf et al., *J. Med. Chem.* 45, 3813 (2002)). Furthermore, in a recent study, it has been shown that compounds of this type reduce food intake and also weight gain in obese mice (Wang et al. *Diabetologia* 49, 1333 (2006));

triazoles have shown that they improve metabolic syndrome and slow down the progression of atherosclerosis in mice (Hermanowski-Vosatka et al., *J. Exp. Med.* 202, 517 (2005)).

B. Cognition and Dementia

Slight cognitive problems are common phenomena in elderly individuals and can, in the end, result in the progression of dementia. In the case of elderly humans just as in the case of aged animals, inter-individual differences for general cognitive functions have been linked to differences in long-term exposure to glucocorticoids (Lupien et al., *Nat. Neurosci.* 1, 69, (1998)). Moreover, dysregulation of the HPA (hypothalamic-pituitary-adrenal) axis resulting in chronic exposure of certain sub-regions of the brain to glucocorticoids has been proposed as contributing to the decline of cognitive functions (McEwen et al., *Curr. Opin, Neurobiol.* 5, 205, 1995). 11βHSD1 is abundant in the brain and is expressed in many sub-regions, including the hypothalamus, the frontal cortex and the cerebellum (Sandeep et al., *Proc. Natl. Acad. Sci.* 101, 6734 (2004)). Mice deficient in 11γHSD1 are protected against glucocorticoid-associated hypothalamic dysfunctions which are related to aging (Yau et al., *Proc. Natl. Acad. Sci.* 98, 4716, (2001)). Furthermore, in studies in humans, it has been shown that the administration of carbenoxolone improves verbal fluidity and verbal memory in elderly individuals (You et al., *Proc. Natl. Acad. Sci.* 98, 4716 (2001), Sandeep et al., *Proc. Natl. Acad. Sci.* 101, 6734 (2004)). Finally, the use of selective 11βHSD1 inhibitors of triazole type has shown that they prolong memory retention in aged mice (Rocha et al., Abstract 231 *ACS meeting*, Atlanta, 26-30 Mar. 2006).

C. Intraocular Pressure

Glucocorticoids can be used topically or systemically for a large variety of pathological conditions of clinical ophthalmology. One particular complication of these treatments is glaucoma induced by the use of corticosteroids. This pathological condition is characterized by elevated intraocular pressure (IOP). In the most serious cases and for the non-treated forms, the IOP may result in a partial loss of visual field and possibly in a complete loss of sight. The IOP is the result of an imbalance between the production of aqueous humor and the drainage thereof. The aqueous humor is produced in the nonpigmented epithelial cells and drainage is carried out through the cells of the trabecular network. 11βHSD1 is localized in the nonpigmented epithelial cells and its function is clearly the amplification of glucocorticoid activity in these cells (Stokes et al., *Invest. Ophthalmol, Vis. Sci.* 41, 1629 (2000)). This notion is confirmed by the observation that the concentration of free cortisol is in great excess relative to cortisone in the aqueous humor (14/1 ratio). The functional activity of 11βHSD1 in the eyes has been evaluated by studying the action of carbenoxolone in healthy volunteers. After seven days of treatment with carbenoxolone, the IOP is reduced by 18% (Rauz et al., *Invest. Ophtamol. Vis. Sci.* 42, 2037 (2001)). The inhibition of 11βHSD1 in the eyes is therefore predicted to reduce the local concentration of glucocorticoids and the IOP, producing a beneficial effect in the treatment of glaucoma and of other sight disorders.

D. Hypertension

Hypertensive substances derived from adipocytes, such as leptin and angiotensinogen, have been proposed as being key elements in obesity-related hypertensive pathological conditions (Wajchenberg at al., *Endocr. Rev.* 21, 697 (2000)), Leptin, which is secreted in excess in transgenic aP2-11βHSD1 mice (Masuzaki et al., *J. Clinical Invest.* 112, 83 (2003)), can activate various networks of sympathetic neuronal systems, including those which regulate arterial pressure (Matsuzawa et al., *Acad. Sci.* 892, 146 (1999)). Furthermore, the renin-angiotensin system (RAS) has been identified as being a determining pathway in the variation of arterial pressure. Angiotensinogen, which is produced in the liver and the adipose tissue, is a key substance for renin and is responsible for activation of the RAS. The plasma angiotensinogen level is significantly elevated in transgenic aP2-11βHSD1 mice, as are those of angiotensin II and of aldosterone (Masuzaki et al., *J. Clinical Invest.* 112, 83 (2003)); these elements produce an elevated arterial pressure. The treatment of these mice with low doses of an angiotensin II receptor antagonist abolishes this hypertension (Masuzaki et al., *J. Clinical Invest.* 112, 83 (2003)). This information illustrates the importance of the local activation of glucocorticoids in adipose tissue and the liver, and suggests that this hypertension may be caused or exacerbated by the activity of 11βHSD1 in these tissues. The inhibition of 11βHSD1 and the reduction of the glucocorticoid level in adipose tissue and/or in the liver is therefore predicted as having a beneficial role for the treatment of hypertension and associated cardiovascular pathological conditions.

E. Osteoporosis

Skeletal development and bone functions are also regulated by the action of glucocorticoids. 11βHSD1 is present in osteoclasts and osteoblasts. The treatment of healthy volunteers with carbenoxolone has shown a decrease in bone resorption markers without any change in bone formation markers (Cooper et al., Bone, 27, 375 (2000)). The inhibition of 11βHSD1 and the reduction of the glucocorticoid level in the bones could therefore be used as a mechanism of protection in the treatment of osteoporosis.

Tropane urea derivatives which modulate 11betaHSD1 activity have now been found.

A subject of the present invention is compounds corresponding to formula (I):

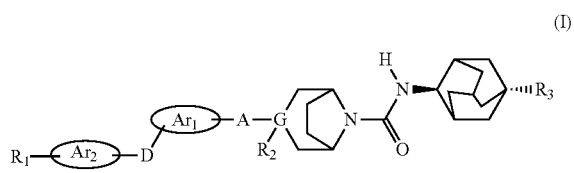

in which
A is a bond or an —O—(CH$_2$)$_n$— group with n being a number equal to 0 or 1,
D is a bond or an oxygen atom,
G is a carbon or nitrogen atom,
Ar1 is an aryl or heteroaryl group,
Ar2 is an aryl or heteroaryl or heterocycloalkyl group.
R1 is a hydrogen atom, or a (C1-C6)alkyl, —SO$_2$—(C1-C6)alkyl, —SO$_2$-halo(C1-C6)alkyl, (C1-C6)alkoxy or —Si(alkyl)$_3$ group,
R2 is a hydrogen atom or a hydroxyl group or, when G is a nitrogen atom, R2 is absent,
R3 is a hydroxyl or —C(O)—NH$_2$ group.

Among the compounds described in the present invention, mention may be made of a first group of compounds corresponding to formula (I) in which:
A is a bond or an —O—(CH$_2$)$_n$— group with n being a number equal to 0 or 1,
and/or
G is a carbon or nitrogen atom,
and/or
D is a bond or an oxygen atom,
and/or
Ar1 is an aryl or heteroaryl group,
and/or
Ar2 is an aryl or heteroaryl or heterocycloalkyl group,
and/or
R1 is a hydrogen atom, or a (C1-C6)alkyl, —SO$_2$—(C1-C6)alkyl, —SO$_2$-halo(C1-C6)alkyl, (C1-C6)alkoxy or —Si(alkyl)$_3$ group,
and/or
R2 is a hydrogen atom or a hydroxyl group or, when G is a nitrogen atom, R2 is absent,
and/or
R3 is a hydroxyl or —C(O)—NH$_2$ group.

The compounds of formula (I) can comprise one or more asymmetric carbon atoms. They can therefore exist in the form of enantiomers or of diastereoisomers. When G is a carbon atom, the compounds of formula (I) can exist in endo or exo form. These enantiomers, diastereoisomers, endo or exo form, and also mixtures thereof, including racemic mixtures, form part of the invention.

The compounds of formula (I) can exist in the form of bases or in a form salified with acids or bases, in particular pharmaceutically acceptable acids or bases. Such addition salts form part of the invention.

These salts are advantageously prepared with pharmaceutically acceptable acids, but the salts of other acids that are of use, for example, for purifying or isolating the compounds of formula (I) also form part of the invention.

In the context of the present invention, and unless otherwise mentioned in the text:
the term "halogen atom" is intended to mean: a fluorine, a chlorine, a bromine or an iodine;
the term "alkyl group" is intended to mean; a linear or branched, saturated aliphatic group containing 1 to 6 carbon atoms. By way of examples, mention may be made of methyl, ethyl, propyl, isopropyl, butyl, isobutyl, tert-butyl, pentyl, etc. groups;
the term "heterocycloalkyl group" is intended to mean: a cyclic alkyl group comprising between 3 and 6 carbon atoms and comprising between 1 and 3 heteroatoms, such as nitrogen, oxygen or sulfur. By way of examples, mention may be made of monocyclic heterocycloalkyl groups such as the piperazine, morpholine, etc. group;
the term "alkoxy group" is intended to mean: an —O-alkyl radical where the alkyl group is as defined above;
the term "haloalkyl group" is intended to mean: an alkyl group in which one or more hydrogen atoms has (have) been substituted with a halogen atom. By way of examples, mention may be made of the —CH$_2$—CF$_3$ group;
the term "aryl group" is intended to mean: a cyclic aromatic group comprising between 5 and 6 carbon atoms. By way of examples of aryl groups, mention may be made of the phenyl group;
the term "heteroaryl group" is intended to mean: a cyclic aromatic group comprising between 5 and 6 carbon atoms and comprising between 1 and 3 heteroatoms, such as nitrogen, oxygen or sulfur. By way of examples of heteroaryl groups, mention may be made of the pyridine group or the pyrimidine group.

A first subgroup of compounds of the invention is made up of the compounds of formula (I) in which the substituents of the Ar1 group are in the para-position with respect to one another.

A second subgroup of compounds of the invention is made up of the compounds of formula (I) in which the substituents of the Ar2 group are in the para-position with respect to one another.

A third subgroup of compounds of the invention is made up of the compounds of formula (I) in which Ar1 is a phenyl, pyridine or pyrimidine group.

A fourth subgroup of compounds of the invention is made up of the compounds of formula (I) in which Ar2 is a phenyl, pyridine, piperazine or morpholine group, A fifth subgroup of compounds of the invention is made up of the compounds of formula (I) in which G is a carbon atom.

A sixth subgroup of compounds of the invention is made up of the compounds of formula (I) in which G is a carbon atom and A is an oxygen atom.

A seventh subgroup of compounds of the invention is made up of the compounds of formula (I) in which G is a carbon atom and A is an —O—$(CH_2)_n$— group with n equal to 1.

An eighth subgroup of compounds of the invention is made up of the compounds of formula (I) in which G is a carbon atom and A is a bond.

A ninth subgroup of compounds of the invention is made up of the compounds of formula (I) in which G is a nitrogen atom and R2 is absent.

A tenth subgroup of compounds of the invention is made up of the compounds of formula (I) in which R3 is —C(O)—$NH_2$.

The subgroups defined above, taken separately or in combination, also form part of the invention.

Among the compounds of formula (I) according to the invention, mention may be made of:

Ex1: 3-[4-(4-Methanesulfonylpiperazin-1-yl)phenyl]-8-azabicyclo[3.2.1]octane-8-carboxylic acid (trans-5-hydroxyadamantan-2-yl)amide Ex 2: 3-[4-(Pyridin-2-yloxy)phenyl]-8-azabicyclo[3.2.1]octane-8-carboxylic acid (trans-5-hydroxyadamantan-2-yl)amide Ex3: endo-3-Hydroxy-3-[4-(4-methanesulfonylpiperazin-1-yl)phenyl]-8-azabicyclo-[3.2.1]octane-8-carboxylic acid (trans-5-hydroxyadamantan-2-yl)amide Ex 4: endo-3-Hydroxy-3-[4-(4-methanesulfonylpiperazin-1-yl)phenyl]-8-azabicyclo-[3.2.1]octane-3-carboxylic acid (trans-5-carbamoyladamantan-2-yl)amide Ex5: exo-3-[4-(4-Methanesulfonylpiperazin-1-yl)phenoxy]-8-azabicyclo-[3.2.1]octane-8-carboxylic acid (trans-5-hydroxyadamantan-2-yl)amide Ex6: exo-3-[4-(4-Methanesulfonylpiperazin-1-yl)phenoxy-]8-azabicyclo-[3.2.1]octane-8-carboxylic acid (trans-5-carbamoyladamantan-2-yl)amide Ex7: endo-3-[4-(4-Methanesulfonylpiperazin-1-yl)-phenoxy]-8-azabicyclo-[3.2.1]octane-8-carboxylic acid (trans-5-hydroxyadamantan-2-yl)amide Ex8: exo-3-(4-Morpholin-4-ylphenoxy)-8-azabicyclo[3.2.1]octane-8-carboxylic acid (trans-5-carbamoyladamantan-2-yl)amide Ex9: exo-3-[5-(4-Isopropoxyphenyl)pyridin-2-yloxy]-8-azabicyclo[3.2.1]octane-8-carboxylic acid (trans-5-carbamoyladamantan-2-yl)amide Ex10: exo-3-[5-(4-Methanesulfonylpiperazin-1-yl)pyridin-2-yloxy]-8-azabicyclo-[3.2.1]octane-8-carboxylic acid (trans-5-carbamoyladamantan-2-yl)amide Ex11: exo-3-[5-(4-Methoxyphenyl)pyrimidin-2-yloxy]-8-azabicyclo[3.2.1]octane-8-carboxylic acid (trans-5-hydroxyadamantan-2-yl)amide Ex12: exo-3-[5-(4-Methoxyphenyl)pyrimidin-2-yloxy]-8-azabicyclo[3.2.1]octane-8-carboxylic acid (trans-5-carbamoyladamantan-2-yl)amide Ex13: exo-3-[4-(4-Methanesulfonylpiperazin-1-yl)phenoxymethyl]-8-azabicyclo-[3.2.1]octane-8-carboxylic acid (trans-5-hydroxyadamantan-2-yl)amide Ex14: exo-3-[4-(4-Methanesulfonylpiperazin-1-yl)phenoxymethyl]-8-azabicyclo-[3.2.1]octane-8-carboxylic acid (trans-5-carbamoyladamantan-2-yl)amide Ex15: endo-Hydroxy-3-[4-(4-methanesulfonylpiperazin-1-yl)phenoxymethyl]-8-azabicyclo[3.2.1]octane-8-carboxylic acid (trans-5-hydroxyadamantan-2-yl)amide Ex16: endo-3-Hydroxy-3-[4-(4-methanesulfonylpiperazin-1-yl)phenoxymethyl]-8-azabicyclo[3.2.1]octane-8-carboxylic acid (trans-5-carbamoyladamantan-2-yl)amide Ex17: endo-3-[4-(4-Methanesulfonylpiperazin-1-yl)phenoxymethyl]-8-azabicyclo-[3.2.1]octane-8-carboxylic acid (trans-5-hydroxyadamantan-2-yl)amide Ex18: endo-3-[5-(4-Methanesulfonylpiperazin-1-yl)pyridin-2-yloxymethyl]-8-azabicyclo[3.2.1]octane-8-carboxylic acid (trans-5-hydroxyadamantan-2-yl)amide Ex19: endo-3-[5-(4-Methanesulfonylpiperazin-1-yl)pyridin-2-yloxymethyl]-8-aza-bicyclo[3.2.1]octane-8-carboxylic acid (trans-5-carbamoyladamantan-2-yl)amide Ex20: endo-3-[5-(4-tert-Butylpiperazin-1-yl)pyridin-2-yloxymethyl]-8-azabicyclo-[3.2.1]octane-8-carboxylic acid (trans-5-carbamoyladamantan-2-yl)amide Ex21: endo-3-[5-(4-tert-Butylpiperazin-1-yl)pyridin-2-yloxymethyl]-8-azabicyclo-[3.2.1]octane-8-carboxylic acid (trans-5-hydroxyadamantan-2-yl)amide Ex22: exo-3-[5-(4-Methanesulfonylpiperazin-1-yl)pyridin-2-yloxymethyl]-8-aza-bicyclo[3.2.1]octane-8-carboxylic acid (trans-5-carbamoyladamantan-2-yl)amide Ex23: exo-3-[5-(4-tert-Butyl-piperazin-1-yl)pyridin-2-yloxymethyl]-8-azabicyclo-[3.2.1]octane-8-carboxylic acid (trans-5-hydroxyadamantan-2-yl)amide Ex24: exo-3-[5-(4-tert-Butylpiperazin-1-yl)pyridin-2-yloxymethyl]-8-azabicyclo-[3.2.1]octane-8-carboxylic acid (trans-5-carbamoyladamantan-2-yl)amide Ex25: 3-[5-(4-Methanesulfonylpiperazin-1-yl)pyridin-2-yl]-3,8-diazabicyclo-[3.2.1]octane-8-carboxylic acid (trans-5-hydroxyadamantan-2-yl)amide Ex26: 3-[5-(4-Methanesulfonylpiperazin-1-yl)pyridin-2-yl]-3,8-diazabicyclo-[3.2.1]octane-8-carboxylic acid (trans-5-carbamoyladamantan-2-yl)amide Ex27: exo-3-[5-(4-Trimethylsilanylphenyl)pyridin-2-yloxy]-8-azabicyclo[3.2.1]octane-8-carboxylic acid (5-carbamoyladamantan-2-yl)amide In what follows, the term "protective group" (PG) is intended to mean a group which makes it possible, on the one hand, to protect a reactive function, such as a hydroxyl or an amine, during a synthesis and, on the other hand, to regenerate the reactive function intact at the end of the synthesis. Examples of protective groups and also methods of protection and deprotection are given in "Protective Groups in Organic Synthesis", Green et al., $3^{rd}$ Edition (John Wiley & Sons, Inc., New York).

The term "leaving group" (Lg) is intended to mean, in what follows, a group which is bonded to a molecule or a compound by a bond and which can be easily split from said molecule or from said compound by hydrolytic cleavage of said bond, with a departure of an electron pair. This group can thus be easily replaced with another group, for example during a substitution reaction. Such leaving groups are, for example, halogens or an activated hydroxyl group, such as a mesyl, tosyl, triflate, acetyl, etc. Examples of leaving groups and also references for the preparation thereof are given in "Advances in Organic Chemistry", J. March, $3^{rd}$ Edition, Wiley Interscience, p. 310-316.

In accordance with the invention, the compounds of formula (I) can be prepared according to the following process.

Scheme 1: The compounds (I) described in the invention can be synthesized according to the following general procedure described in scheme 1:

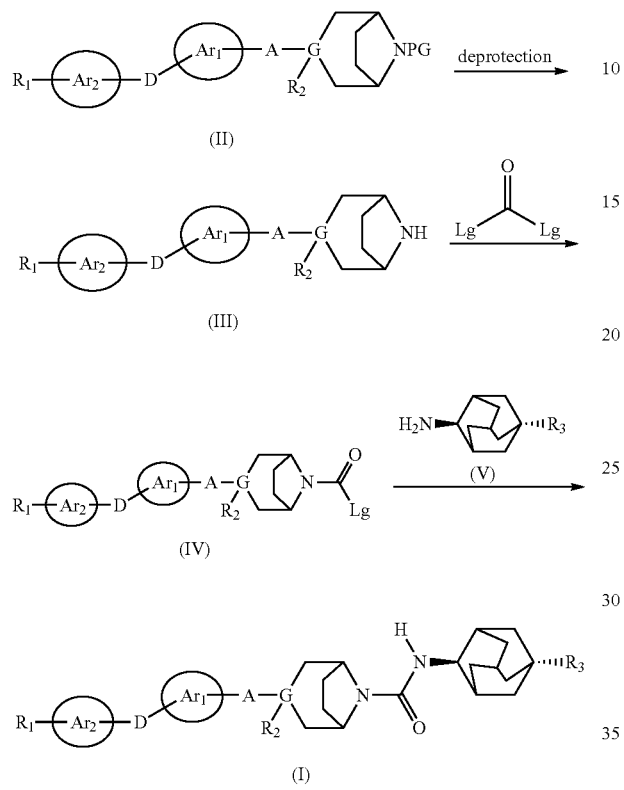

The amine function of the compounds (II) is deprotected as described in Green. T. W., and Wutz P. G. M., *Protective groups in organic synthesis* (1999) under acid conditions such as HCl in dioxane or trifluoroacetic acid in a solvent such as dichloromethane in order to cleave a t-butoxycarbonyl group. Pd/C under hydrogen or in the presence of ammonium formate in a solvent such as methanol can be used to cleave a benzyl group. 1-Chloroethyl chloroformate in a solvent such as dichloroethane can be used to cleave a methyl group. The compounds (III) obtained react with a carbonyl having two leaving groups Lg (for example, a chlorine atom, a trichloromethoxy group, a para-nitrophenyl group, an imidazole group or a methylimidazolium group) in the presence of a base such as triethylamine or sodium bicarbonate, in a solvent such as dichloromethane or tetrahydrofuran, and at a temperature ranging from ambient temperature to 80° C. The compounds of formula (I) are then obtained by coupling between the activated derivatives (IV) and the amines (V) optionally in the presence of a base such as triethylamine or potassium carbonate, in a solvent such as a polar solvent, for example tetrahydrofuran, dichloromethane, acetonitrile, dimethylformamide or water, at a temperature ranging from ambient temperature to 100° C.

The heterocycles of formula (V) are commercially available or can be prepared by methods described in the literature (for example, WO 2007/077949, US 2005/0215784 A1, US 2005/0245745 A1).

Scheme 2: The compounds (II) for which A is a bond, G is —C—, $R_2$ is —H and D is a bond or —O— are hereinafter referred to as compounds (IIa) and can be synthesized according to scheme 2 below:

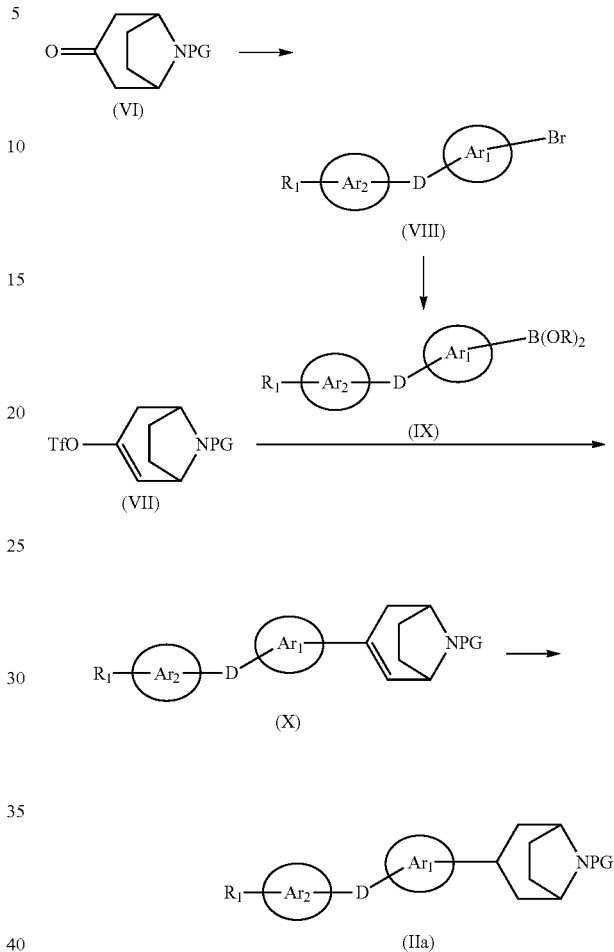

The commercial tropanone (VI) protected on the nitrogen can give the corresponding vinyl triflate (VII) by reaction with a strong base such as lithium bis(trimethylsilyl)amide in a solvent such as THF or DME at a temperature ranging from −78° C. to ambient temperature. The compounds (X) can be obtained by Suzuki coupling in the presence of an organometallic catalyst such as a palladium derivative, for instance tetrakis(triphenylphosphine)palladium, and of a base such as $Na_2CO_3$ or $Cs_2CO_3$ or potassium fluoride in a solvent such as toluene. DME or THF, at temperatures ranging from ambient temperature to 115° C., between the compound (VII) and the compound (IX). The compounds (IX) can be obtained by organometallic coupling between the compound (VIII) and bis(pinacolato)diboron in the presence of a catalyst such as a palladium derivative, for instance dichloro(diphenylphosphino-ferrocene)palladium, and of a base such as potassium acetate in a solvent such as DME or THF at temperatures ranging from ambient temperature to 90° C. The reduction of the double bond of the compounds (X) can be carried out in the presence of a catalyst such as Pd/C in the presence of hydrogen, in a solvent such as methanol or ethyl acetate, to give the compounds (IIa).

Scheme 3a: The compounds (II) for which A is a bond, D is a bond, G is ——C——, R$_2$ is ——OH and Ar2 is a heterocycloalkyl group, or for which A is ——O——(CH$_2$)$_n$—— (n=0 or 1), D is a bond, G is ——C——, R$_2$ is H and Ar2 is a heterocycloalkyl group, or for which A is a bond, G is an ——N——, R$_2$ does not exist and Ar2 is a heterocycloalkyl group, are hereinafter referred to a compounds (IIb) and can be obtained according to scheme 3a below:

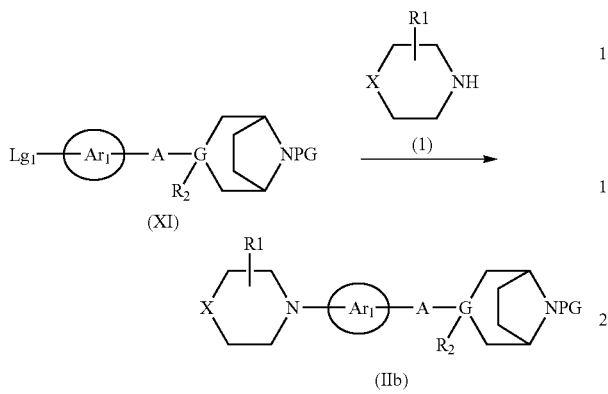

The compounds (XI) where Lg1 is a leaving group, such as a bromine or iodine atom or a triflate, can be used in an organometallic coupling reaction, for instance Buchwald-Hartwig amination, in the presence of a secondary amine (1) and of palladium-derived catalysts, such as tris(dibenzylideneacetone)dipalladium or 2'-(dimethylamino)-2-biphenylyl-palladium(II) chloride dinorbornylphosphine complex, of a ligand such as S-Phos and of a base such as sodium t-butoxide or potassium phosphate in a solvent or mixture of solvents, such as dioxane, toluene, tetrahydrofuran or DME, at temperatures ranging from ambient temperature to 115° C.

Scheme 3B: The compounds (II) for which A is a bond, D is a bond, G is ——C——, R$_2$ is ——OH and Ar2 is an aryl or heteroaryl, or for which A is ——O——(CH$_2$)$_n$—— ( n = 0 or 1), D is a bond, G is ——C——, R$_2$ is H and Ar2 is an aryl or heteroaryl, or for which A is a bond, G is an ——N——, R$_2$ does not exist and Ar2 is an aryl or heteroaryl, are hereinafter referred to as compounds (IIb') and can be obtained according to scheme 3b below:

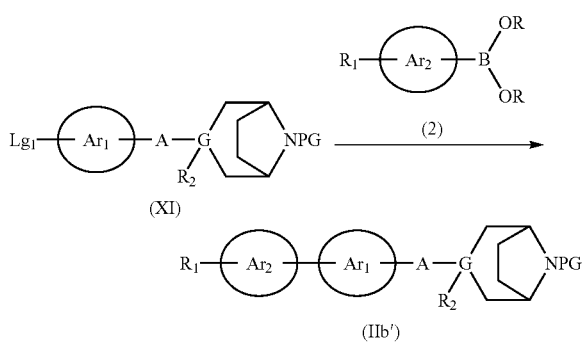

The compounds (XI) where Lg1 is a leaving group, such as a bromine or iodine atom or a triflate, can be used in an organometallic coupling reaction, for instance Suzuki coupling, in the presence of a boron derivative (2) (with R being a hydrogen or together forming an —OCMe$_2$CMe$_2$O—) and of an organometallic catalyst, such as a palladium derivative, optionally in the presence of a phosphine, such as tetrakis (triphenylphosphine)palladium, and of a base such as Na$_2$CO$_3$, cesium carbonate or potassium fluoride, in a solvent such as toluene. DME or THF, at temperatures ranging from ambient temperature to 115° C.

Scheme 4: The compounds (XI) for which A is a bond, G is ——C——, D is a bond and R$_2$ is ——OH are hereinafter referred to as compounds (XIa) and can be obtained according to scheme 4 below:

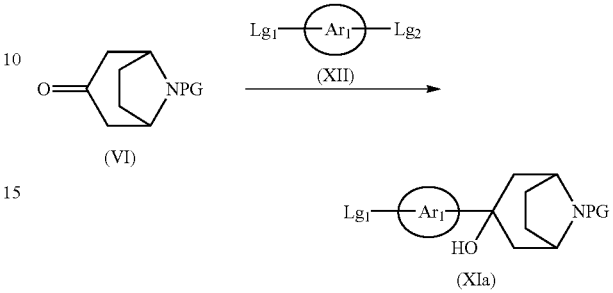

The compounds (XII) where Lg1 and Lg2 are a leaving group such as a halogen atom, for example a bromine atom, and Ar1 is an aryl or heteroaryl nucleus, can react with a strong base, such as butyllithium or lithium bis(trimethylsilyl)amide, in a solvent such as THF or hexane, at a temperature ranging between −78° C. and ambient temperature, so as to form the corresponding monoanion. This can give, in the presence of the commercial tropanone (VI), in a solvent such as THF or hexane at a temperature ranging between −78° C. and ambient temperature, the compounds (XIa).

Scheme 5: The compounds (XI) for which A is ——O——(CH$_2$)$_n$—— (n=0 or 1), G is ——C—— and R$_2$ is ——H are hereinafter referred to as compounds (XIb) and can be obtained according to scheme 5 below:

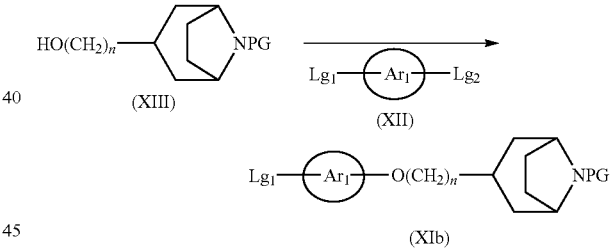

The compounds (XIII) can react with the compound (XU) where Lg2 is a leaving group, such as a fluorine atom, and Ar1 is an aryl or heteroaryl nucleus, in the presence of a strong base such as sodium hydride or potassium t-butoxide, in a solvent such as NMP or DMF, at temperatures ranging from 0° to 130° C., to give the compounds (XIb).

Scheme 6: The compounds (XI) for which A is a bond, G is ——N—— and R$_2$ is absent are hereinafter referred to as compounds (XIc) and can be obtained according to scheme 6 below:

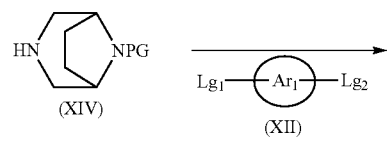

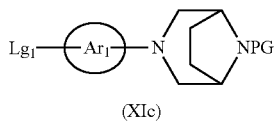

(XIc)

The 3,8-diazabicyclo[3.2.1]octane (XIV) protected on position 8 can give the compounds (XIc) in the presence of the compounds (XII) where Lg2 is a leaving group, such as a bromine atom, and Ar1 is an aryl or heteroaryl nucleus, via a Buchwald-Hartwig amination reaction as described above.

Scheme 7: Alternatively, the compounds (II) for which A is
—O—(CH$_2$)$_n$— (n=0 or 1), G is —C—, R$_2$ is —H
and D is a bond are hereinafter referred to as compounds (IIc) and can be obtained according to scheme 7 below:

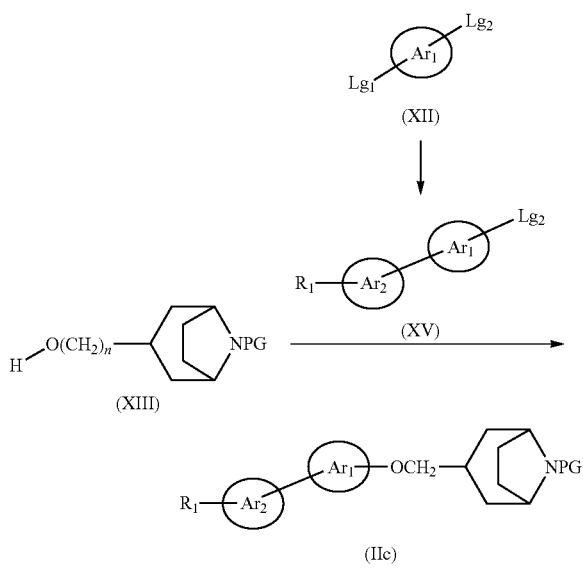

(IIc)

The compounds (XIII) can react with the compounds (XV) where Lg2 is a leaving group, such as a halogen atom, for instance a fluorine atom, in the presence of a strong base such as sodium hydride or potassium tert-butoxide, in a solvent such as DMF or NMP, at temperatures ranging from 0° C. to 130° C., to give the compound (IIc). The compounds (XV) may be commercially available or synthesized via reactions such as Buchwald-Hartwig amination under conditions as described above.

Scheme 8: The compounds (II) for which A is an —O—CH$_2$—, G is —C—, R$_2$ is —OH and D is a bond are hereinafter referred to as compounds (IId) and can be obtained according to scheme 8 below:

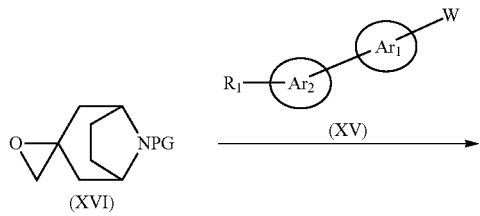

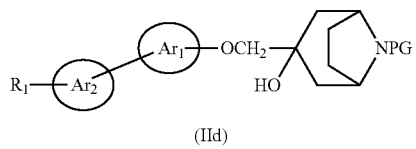

(IId)

The compounds (XVI) obtained according to the procedure described in the literature (*J. Het. Chem.* (1968), pp 467) can react with the compounds (XV) where W is an OH group, in the presence of a strong base such as sodium hydride or sodium hydroxide, in a polar solvent such as DMF, dimethyl sulfoxide or water, at a temperature ranging from 0° C. to 130° C., to give the compounds (IId).

In schemes 1 to 8, the starting compounds and the reactants, when the method for preparing them is not described, are commercially available or described in the literature, or else can be prepared according to methods which are described therein or which are known to those skilled in the art.

According to another of the aspects of the invention, a subject thereof is also the compounds of formulae (IX), (X), (XI), (XIa), (XIb), (XIc), (II), (IIa), (IIb), (IIb'), (IIc), (IId), (III) and (IV). These compounds are of use as intermediates for the synthesis of the compounds of formula (I).

The following examples describe the preparation of certain compounds in accordance with the invention. These examples are not limiting and merely illustrate the present invention. The numbers of the compounds exemplified refer back to those given in the table hereinafter, which illustrates the chemical structures and the physical properties of some compounds according to the invention.

The following abbreviations and empirical formulae are used:

| | |
|---|---|
| ° C. | degree Celsius |
| Cs$_2$CO$_3$ | cesium carbonate |
| DIAD | 1,1'-(azodicarbonyl)dipiperidine |
| DME | dimethoxyethane |
| DMF | dimethylformamide |
| DMSO | dimethyl sulfoxide |
| h | hour(s) |
| HCl | hydrochloric acid |
| K$_2$CO$_3$ | potassium carbonate |
| KHSO$_4$ | potassium bisulfate |
| LC/MS | liquid chromatography/mass spectrometry |
| M | molar |
| MgSO$_4$ | magnesium sulfate |
| MHz | megaHertz |
| min | minute(s) |
| ml | milliliter(s) |
| mmol | millimol(s) |
| N | normal |
| Na$_2$CO$_3$ | sodium carbonate |
| NaHCO$_3$ | sodium hydrogen carbonate |
| NMP | N-methylmorpholine |
| P$_2$O$_5$ | phosphorus pentoxide |
| ppm | parts per million |
| psi | pounds per square inch |
| S-Phos | 2-dicyclohexylphosphino-2',6'-dimethoxybiphenyl |
| tBu | tert-butyl |
| XantPhos | 9,9-dimethyl-4,5-bis(diphenylphosphino)xanthene |

EXAMPLE 1

3-[4-(4-Methanesulfonylpiperazin-1-yl)phenyl]-8-azabicyclo[3.2.1]octane-8-carboxylic acid (trans-5-hydroxyadamantan-2-yl)amide (Compound No. 1)

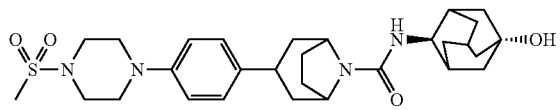 [SMILES: CS(=O)(=O)N1CCN(c2ccc(C3CC4CCC(C3)N4C(=O)N[C@H]3C4CC5CC3C[C@@](O)(C5)C4)cc2)CC1]

1.1/3-Trifluoromethanesulfonyloxy-8-azabicyclo[3.2.1]oct-2-ene-8-carboxylic acid tert-butyl ester 3-Oxo-8-azabicyclo[3.2.1]octane-8-carboxylic acid tert-butyl ester (5 g, 22.2 mmol) is placed in 24 ml of anhydrous THF and the solution is cooled to −70° C. under nitrogen, 1N lithium bis(trimethylsilyl)amide in THF (24.4 ml, 24.4 mmol) is added dropwise. After stirring for 45 min at −70° C., N-phenyltrifluoromethane-sulfonimide (8.7 g, 24.4 mmol) placed in 25 ml of anhydrous THF is added dropwise. The temperature of the reaction medium is left to rise slowly. Stirring is maintained for 16 h at ambient temperature. After concentration to dryness, the crude product obtained is chromatographed on silica gel, elution being carried out with a cyclohexane/ether mixture (90/10). 10.2 g of expected 3-trifluoromethanesulfonyloxy-8-azabicyclo[3.2.1]oct-2-ene-8-carboxylic acid tert-butyl ester are obtained.

[M+H⁺]=258 (—OtBu)

1.2/1-(4-Bromophenyl)-4-methanesulfonylpiperazine 1-(4-Bromophenyl)piperazine (5 g, 20.7 mmol) is placed in 104 ml of dichloromethane and then triethylamine (4.34 ml, 31.1 mmol) is added, followed, dropwise, by methanesulfonyl chloride (1.93 ml, 24.9 mmol). Stirring is maintained for 16 h. After the addition of 30 ml of water and stirring, the organic phase is washed with a saturated aqueous sodium chloride solution, dried over MgSO$_4$ and concentrated. 6.6 g of expected 1-(4-bromophenyl)-4-methanesulfonylpiperazine are obtained.

[M+H⁺]=319

1.3/1-Methanesulfonyl-4-[4-(4,4,5,5-tetramethyl[1,3,2]dioxaborolan-2-yl)-phenyl]piperazine 1-(4-Bromophenyl)-4-methanesulfonylpiperazine (2 g, 6.3 mmol) is placed in 42 ml of DME. bis(Pinacolato)diboron (1.91 g, 7.52 mmol), potassium acetate (1.85 g, 18.8 mmol) and dichloro(diphenylphosphinoferrocene)palladium (0.511 g, 0.63 mmol) are added. The reaction medium is refluxed for 16 h. After hydrolysis and extraction with ethyl acetate, the organic phase is filtered on Celite®, washed with a saturated aqueous sodium chloride solution, dried over MgSO$_4$ and concentrated to dryness. The crude product obtained is chromatographed on silica gel, elution being carried out with a dichloromethane/ethyl acetate mixture (95/5). 1.8 g of 1-methanesulfonyl-4-[4-(4,4,5,5-tetramethyl[1,3,2]dioxaborolan-2-yl)phenyl]piperazine are obtained.

[M+H⁺]=367

1.4/3-[4-(4-Methanesulfonylpiperazin-1-yl)phenyl]-8-azabicyclo[3.2.1]oct-2-ene-8-carboxylic acid tert-butyl ester 1-Methanesulfonyl-4-[4-(4,4,5,5-tetramethyl[1,3,2]-dioxaborolan-2-yl)phenyl]-piperazine (1.8 g, 4.9 mmol) and 3-trifluoromethanesulfonyloxy-8-azabicyclo[3.2.1]-oct-2-ene-8-carboxylic acid tert-butyl ester (3.8 g, 5.9 mmol) are placed in 35 ml of DME and 6.14 ml of a 2N aqueous solution of K$_2$CO$_3$. After degassing with nitrogen, tetrakis(triphenylphosphine)palladium (1.136 g, 0.98 mmol) is added. The reaction medium is refluxed for 6 h. After hydrolysis and addition of ethyl acetate, the reaction medium is filtered on Celite®. The aqueous phase is then extracted with ethyl acetate. The organic phase is washed with a saturated aqueous solution of NaHCO$_3$ and than with water. After drying over MgSO$_4$ and concentration to dryness, the crude product obtained is chromatographed on silica gel, elution being carried out with a gradient of ethyl acetate in dichloromethane ranging from 0% to 20%. 0.83 g of 3-[4-(4-methanesulfonylpiperazin-1-yl)phenyl]-8-azabicyclo[3.2.1]oct-2-ene-8-carboxylic acid tert-butyl ester is obtained.

[M+H⁺]=448

1.5/3-[4-(4-Methanesulfonylpiperazin-1-yl)phenyl]-8-azabicyclo[3.2.1]octane-8-carboxylic acid tert-butyl ester 3-[4-(4-Methanesulfonylpiperazin-1-yl)phenyl]-8-azabicyclo[3.2.1]oct-2-ene-8-carboxylic acid tert-butyl ester (0.83 g, 1.85 mmol) is solubilized in 93 ml of methoxyethanol. Palladium-on-carbon at 10% (0.395 g) is then added. The reaction medium is stirred for 5 h under 30 psi of hydrogen at 25° C. After filtration on Celite® and concentration, 0.76 g of expected 3-[4-(4-methanesulfonylpiperazin-1-yl)phenyl]-8-azabicyclo[3.2.1]octane-8-carboxylic acid tert-butyl ester is obtained.

[M+H⁺]=450

1.6/3-[4-(4-Methanesulfonylpiperazin-1-yl)phenyl]-8-azabicyclo[3.2.1]octane

3-[4-(4-Methanesulfonylpiperazin-1-yl)phenyl]-8-azabicyclo[3.2.1]octane-8-carboxylic acid tert-butyl ester (0.758 g, 1.69 mmol) is solubilized in 158 ml of dichloromethane. 4N HCl in dioxane (4.2 ml, 16.8 mmol) is then added. After stirring for 16 h at ambient temperature, the reaction medium is concentrated, taken up with water, and washed with ethyl acetate. The pH of the aqueous phase is then adjusted to 10 with a 5N aqueous solution of sodium hydroxide. After extraction with dichloromethane, and washing with water and then with a saturated aqueous sodium chloride solution, the organic phase is dried over MgSO$_4$ and then concentrated to dryness. 0.51 g of expected 3-[4-(4-methanesulfonylpiperazin-1-yl)phenyl]-8-aza-bicyclo[3.2.1]octane is obtained, which is subsequently used as it is.

[M+H⁺]=350

1.7/3-[4-(4-Methanesulfonylpiperazin-1-yl)phenyl]-8-azabicyclo[3.2.1]octane-8-carboxylic acid (trans-5-hydroxyadamantan-2-yl)amide 3-[4-(4-Methanesulfonylpiperazin-1-yl)phenyl]-8-azabicyclo[3.2.1]octane (0.26 g, 0.74 mmol) is solubilized in 10 ml of dichloromethane. Diisopropylethylamine (0.25 ml, 1.49 mmol) is added. The reaction medium is placed at 0° C. under nitrogen. Triphosgene (0.11 g, 0.37 mmol) is added, Stirring is maintained for 4 h at ambient temperature. After having again added diisopropylethylamine (0.12 ml, 0.74 mmol) and 10 ml of anhydrous DMF, trans-4-aminoadamantan-1-ol (0.137 g, 0.82 mmol) is added. After stirring for 24 h, the reaction medium is heated at 50° C. for 16 h. Dichloromethane and water are then added. After extraction, the organic phase is washed with water and then with a saturated aqueous sodium chloride solution. It is dried over $MgSO_4$ and then concentrated to dryness. The crude product obtained is taken up with acetonitrile and triturated. The insoluble material is rinsed with pentane and filter-dried. 0.10 g of expected 3-[4-(4-methanesulfonylpiperazin-1-yl)phenyl]-8-azabicyclo[3.2.1]octane-8-carboxylic acid (trans-5-hydroxyadamantan-2-yl)amide is obtained.

Melting point=250° C.; $[M+H^+]=543$ $^1$H NMR (400 MHz, DMSO-d6) δ ppm 7.1 (m, 2H), 6.9 (m, 2H), 5.85 (m, 1H), 4.36 (bs, 1H), 4.3 (bs, 2H), 3.7 (m, 1H), 3.3 to 3.15 (m, 8H), 3.0 (m, 1H), 2.9 (s, 3H), 2.5-2.25 (m, 2H), 2.1-1.25 (m, 19H).

EXAMPLE 2

3-[4-(Pyridin-2-yloxy)phenyl]-8-azabicyclo[3.2.1]octane-8-carboxylic acid (trans-5-hydroxyadamantan-2-yl)amide (Compound No. 2)

2.1/2-(4-Bromophenoxy)pyridine

4-Bromophenol (2 g, 11.5 mmol) is placed in 10 ml of anhydrous DMF under nitrogen. Sodium hydride (0.51 g, 127 mmol) is added. After stirring for 20 min at ambient temperature, 2-fluoropyridine (1.05 ml, 12.1 mmol) is added and the reaction medium is heated at 105° C. for 7 h. After hydrolysis, the pH is adjusted to 8 with a 1N aqueous solution of HCl. The reaction medium is then extracted with ethyl acetate. The organic phase is washed with a saturated aqueous sodium chloride solution, dried over $MgSO_4$ and concentrated to dryness. The crude product obtained is chromatographed on silica gel, elution being carried out with a gradient of ethyl acetate in heptane ranging from 0% to 30%. 2.22 g of expected 2-(4-bromo-phenoxy)pyridine are obtained, $[M+H^+]=250$ 2.2/2-[4-(4,4,5,5-Tetramethyl[1,3,2]dioxaborolan-2-yl)phenoxy]pyridine According to a procedure identical to that described in step 1.3, starting from 2-(4-bromophenoxy)pyridine (1.2 g, 4.8 mmol), 0.63 g of expected 2-[4-(4,4,5,5-tetra-methyl[1,3,2]dioxaborolan-2-yl)phenoxy]pyridine is obtained after chromatography on silica gel, elution of the crude product obtained being carried out with a gradient of ethyl acetate in dichloromethane ranging from 0% to 4%.

$[M+H^+]=297$ 2.3/3-[4-(Pyridin-2-yloxy)phenyl]-8-azabicyclo[3.2.1]oct-2-ene-8-carboxylic acid tert-butyl ester 2-[4-(4,4,5,5-Tetramethyl[1,3,2]dioxaborolan-2-yl)phenoxy]pyridine (0.62 g, 2.1 mmol), 3-trifluoromethanesulfonyloxy-8-azabicyclo[3.2.1]oct-2-ene-8-carboxylic acid tert-butyl ester (0.75 g, 2.1 mmol) (intermediate 1), tetrakis(triphenylphosphine)-palladium (0.24 g, 0.21 mmol) and lithium chloride (0.107 g, 2.52 mmol) are placed in 10 ml of DME and 2.6 ml of a 2N aqueous solution of $K_2CO_3$. The reaction medium is refluxed for 16 h. After hydrolysis and extraction with ethyl acetate, the organic phase is dried over $MgSO_4$ and concentrated to dryness. The crude product obtained is chromatographed on silica gel, elution being carried out with a gradient of ethyl acetate in heptane ranging from 0% to 30%. 0.45 g of expected 3-[4-(pyridin-2-yl-oxy)phenyl]-8-azabicyclo[3.2.1]oct-2-ene-8-carboxylic acid tert-butyl ester is obtained.

$[M+H^+]=379$ 2.4/3-[4-(Pyridin-2-yloxy)phenyl]-8-azabicyclo[3.2.1]octane-8-carboxylic acid tert-butyl ester According to a procedure identical to that described in step 1.5, starting from 3-[4-(pyridin-2-yloxy)phenyl]-8-azabicyclo[3.2.1]oct-2-ene-8-carboxylic acid tert-butyl ester (0.45 g, 0.89 mmol), 0.36 g of expected 3-[4-(pyridin-2-yloxy)phenyl]-8-aza-bicyclo[3.2.1]octane-8-carboxylic acid tert-butyl ester is obtained by chromatographing on silica gel, elution of the crude product obtained being carried out with a gradient of methanol in dichloromethane ranging from 0% to 2%.

$[M+H^+]=381$ 2.5/3-[4-(Pyridin-2-yloxy)phenyl]-8-azabicyclo[3.2.1]octane

According to a procedure identical to that described in step 1.6, starting from 3-[4-(pyridin-2-yloxy)phenyl]-8-azabicyclo[3.2.1]octane-8-carboxylic acid tert-butyl ester (0.34 g, 0.9 mmol), 0.235 g of expected 3-[4-(pyridin-2-yloxy)phenyl]-8-azabicyclo[3.2.1]octane is obtained after concentration to dryness and treatment with a saturated aqueous solution of $NaHCO_3$, extraction with ethyl acetate, washing with a saturated aqueous sodium chloride solution, drying over $MgSO_4$ and concentration to dryness.

$[M+H^+]=281$ 2.6/3-[4-(Pyridin-2-yloxy)phenyl]-8-azabicyclo[3.2.1]octane-8-carboxylic acid (trans-5-hydroxyadamantan-2-yl)amide According to a procedure identical to that described in step 1.7, starting from 3-[4-(pyridin-2-yloxy)phenyl]-8-azabicyclo[3.2.1]octane (0.24 g, 0.84 mmol), 0.054 g of expected 3-[4-(pyridin-2-yloxy)phenyl]-8-azabicyclo[3.2.1]octane-8-carboxylic acid (trans-5-hydroxyadamantan-2-yl)amide is obtained by chromatographing the crude product obtained on silica gel, elution being carried out with a gradient of methanol/aqueous ammonia in dichloromethane ranging from 100/0/0 to 9/1/0.1 (dichloromethane/methanol/aqueous ammonia).

Melting point=103° C.; $[M+H^+]=474$ $^1$H NMR (400 MHz, DMSO-d6) δ ppm 8.15 (m, 1H), 7.85 (m, 1H), 7.25 (m, 1H), 7.2 (m, 1H), 7.1 (m, 1H), 7.05-6.95 (m, 4H), 5.85 (dd, J=18 and 6 Hz, 1H), 4.35 (m, 3H), 3.7 (m, 1H), 3.15 (m, 1H), 2.4 (m, 1H), 2.1-1.15 (m, 19H).

EXAMPLE 3 endo-3-Hydroxy-3-[4-(4-methanesulfonylpiperazin-1-yl)phenyl]-8-azabicyclo-[3.2.1]octane-8-carboxylic acid (trans-5-hydroxyadamantan-2-yl)amide (Compound No. 3)

3.1/8-Benzyl-3-(4-bromophenyl)-8-azabicyclo[3.2.1]octanendo-3-ol

Dibromobenzene (1.09 g, 4.64 mmol) is placed in 8 ml of anhydrous THF under nitrogen at −70° C. 2.5M n-butyllithium in hexane (1.86 ml, 4.64 mmol) is added. Stirring is maintained for 1 h at −70° C. 8-Benzyl-8-azabicyclo[3.2.1] octan-3-one (0.5 g, 2.32 mmol) dissolved in 2 ml of anhydrous THF is then slowly added. After stirring for 1 h at −70° C., the reaction medium is left to return to ambient temperature and stirring is maintained for 16 h. After hydrolysis and extraction of the reaction medium with ethyl acetate, the organic phase is dried over MgSO$_4$. The crude product obtained is chromatographed on silica gel, elution being carried out with a gradient of methanol in dichloromethane ranging from 0% to 10%. 0.53 g of expected 8-benzyl-3-(4-bromophenyl)-8-azabicyclo[3.2.1]octanendo-3-ol is obtained.
[M+H$^+$]=372

3.2/8-Benzyl-3-[4-(4-methanesulfonylpiperazin-1-yl)phenyl]-8-azabicyclo[3.2.1]-octanendo-3-ol 8-Benzyl-3-(4-bromophenyl)-8-azabicyclo[3.2.1]octanendo-3-ol (1.73 g, 4.66 mmol) is placed in 23 ml of DME under nitrogen. 1-Methanesulfonylpiperazine (0.92 g, 5.6 mmol) and the catalyst 2'-(dimethylamino)-2-biphenylyl-palladium(II) chloride dinorbornylphosphine complex (0.26 g, 0.47 mmol) are added. 1N lithium bis(trimethylsilyl)amide in THF (10.3 ml, 10.3 mmol) is added. The reaction medium is refluxed for 16 h. 2'-(Dimethylamino)-2-biphenylyl-palladium(II) chloride dinorbornylphosphine complex catalyst (0.1 g, 0.18 mmol) is again added and stirring at reflux is maintained for a further 6 h. 1N lithium bis(trimethylsilyl) amide in THF (5.1 ml, 5.1 mmol), 2'-(dimethylamino)-2-biphenylyl-palladium(II) chloride dinorbornylphosphine complex catalyst (0.1 g, 0.18 mmol), and 1-methane-sulfonylpiperazine (0.5 g, 3.05 mmol) are then again added. After refluxing for 16 h, hydrolysis is carried out with a saturated aqueous solution of NaHCO$_3$ and then extraction is carried out with ethyl acetate. The organic phase is washed with a saturated aqueous sodium chloride solution and dried over MaSO$_4$. The crude product obtained is chromatographed on silica gel, elution being carried out with a gradient of methanol/aqueous ammonia in dichloromethane ranging from 100/0/0 to 9/1/0.1 (dichloromethane/methanol/aqueous ammonia). 0.67 g of expected 8-benzyl-3-[4-(4-methanesulfonylpiperazin-1-yl)phenyl]-8-azabicyclo[3.2.1] octan-endo-3-ol is obtained.
[M+H$^+$]=456

3.3/3-[4-(4-Methanesulfonylpiperazin-1-yl)phenyl]-8-azabicyclo[3.2.1]octan-endo-3-ol 8-Benzyl-3-[4-(4-methanesulfonylpiperazin-1-yl)phenyl]-8-azabicyclo[3.2]1-octanendo-3-ol (0.67 g, 1.46 mmol) is placed in 15 ml of methanol. Pd/C 10%, ~50% in water (0.17 g) and ammonium formate (0.92 g, 14.6 mmol) are added. The reaction medium is refluxed for 2 h. After the catalyst has been filtered off, the filtrate is concentrated. The crude product obtained is chromatographed on silica gel, elution being carried out with a gradient of methanol/aqueous ammonia in dichloromethane ranging from 100/0/0 to 80/20/2 (dichloromethane/methanol/aqueous ammonia). 0.26 g of expected 3-[4-(4-methanesulfonylpiperazin-1-yl) phenyl]-8-azabicyclo-[3.2.1]octanendo-3-ol is obtained.
[M+H$^+$]=366

3.4/endo-3-Hydroxy-3-[4-(4-methanesulfonylpiperazin-1-yl)phenyl]-8-aza-bicyclo[3.2.1]octane-8-carboxylic acid (trans-6-hydroxyadamantan-2-yl)amide 3-[4-(4-Methanesulfonylpiperazin-1-yl)phenyl]-8-azabicyclo[3.2.1]octanendo-3-ol (0.25 g, 0.68 mmol) is placed in 22 ml of a 50/50 mixture of dichloromethane/saturated aqueous NaHCO$_3$ solution at 0° C. A 20% solution of phosgene in toluene (0.54 ml, 1.5 mmol) is added. After stirring for 1 h 20, a 20% solution of phosgene in toluene (0.16 ml) is again added. After extraction of the aqueous phase with dichloromethane, the organic phase is dried over MgSO$_4$. The crude product obtained is placed in 5.5 ml of anhydrous DMF under nitrogen. Triethylamine (0.19 ml, 1.38 mmol) is added, followed by trans-4-aminoadamantan-1-ol (0.14 g, 0.82 mmol) dissolved in 1.5 ml of anhydrous DMF. The reaction medium is heated at 50° C. for 2 h 30. After hydrolysis with a saturated aqueous NaHCO$_3$ solution, and extraction with ethyl acetate, the organic phase is washed with a saturated aqueous sodium chloride solution and dried over MgSO$_4$. The crude product obtained is chromatographed on silica gel, elution being carried out with a gradient of methanol in dichloromethane ranging from 0% to 10%. 0.075 g of endo-3-hydroxy-3-[4-(4-methanesulfonylpiperazin-1-yl)phenyl]-8-azabicyclo[3.2.1] octane-8-carboxylic acid (trans-5-hydroxyadamantan-2-yl) amide is obtained.
Melting point >250° C.; [M+H$^+$]=559
$^1$H NMR (400 MHz, DMSO-d6) δ ppm: 7.15 (d, J=8.6 Hz, 2H), 6.85 (d, J=8.6 Hz, 2H), 5.85 (d, J=5.8 Hz, 1H), 4.75 (s, 1H), 4.4 (s, 1H), 4.25 (m, 2H), 3.7 (m, 1H),

EXAMPLE 4 endo-3-[4-(4-Methanesulfonylpiperazin-1-yl)phenoxy]-8-azabicyclo[3.2.1]-octane-8-carboxylic acid (trans-5-hydroxyadamantan-2-yl)amide (Compound No. 7)

4.1/endo-3-(4-Bromophenoxy)-8-methyl-8-azabicyclo[3.2.1]octane

Sodium hydride (1.12 g, 46.7 mmol) is placed in 40 ml of anhydrous DMF under nitrogen. Tropine (4.4 g, 31.2 mmol) dissolved in 20 ml of anhydrous DMF is slowly added. The reaction medium is heated at 65° C. for 1 h and than 4-fluorobenzene placed in 10 ml of anhydrous DMF is slowly added. After stirring at 65° C. for 3 h, the medium is hydrolyzed with a water/ice mixture. Extraction is carried out with ethyl acetate. The organic phase is combined, washed with water and then with a saturated aqueous sodium chloride solution and dried over MgSO$_4$. The crude product obtained is taken up with toluene and concentrated to dryness. After recrystallization from a pentane/diethyl ether mixture, 1.87 g of expected endo-3-(4-bromophenoxy)-8-methyl-8-azabicyclo [3.2.1]octane are obtained.
[M+H$^+$]=296

4.2/endo-3-[4-(4-Methanesulfonylpiperazin-1-yl) phenoxy]-8-methyl-8-aza-bicyclo[3.2.1]octane endo-3-(4-Bromophenoxy)-8-methyl-8-azabicyclo[3.2.1] octane (0.5 g, 1.69 mmol), 1-methanesulfonylpiperazine (0.33 g, 2.0 mmol), 2'-(dimethylamino)-2-biphenylyl-palladium(II) chloride dinorbornylphosphine complex catalyst (0.095 g, 0.17 mmol) and potassium phosphate (0.89 g, 4.22 mmol) are placed in 8.5 ml of DME under N$_2$. The reaction medium is stirred at 90° C. for 16 h. After hydrolysis and extraction with ethyl acetate, the organic phase is washed with a saturated aqueous sodium chloride solution and dried over MgSO$_4$. The crude product obtained is chromatographed on silica gel, elution being carried out with a gradient of methanol/aqueous ammonia in dichloromethane ranging from 100/0/0 to 90/10/1 (dichloromethane/methanol/aqueous ammonia). 0.53 g of expected endo-3-[4-(4-methanesulfonylpiperazin-1-yl)phenoxy]-8-methyl-8-azabicyclo[3.2.1]octane is obtained.
[M+H$^+$]=380

4.3/endo-3-[4-(4-Methanesulfonylpiperazin-1-yl)phenoxy]-8-azabicyclo[3.2.1]-octane endo-3-[4-(4-Methanesulfonylpiperazin-1-yl)phenoxy]-8-methyl-8-azabicyclo-[3.2.1]octane (0.91 g, 2.4 mmol) is placed in 4.8 ml of dichloroethane at 0° C. under nitrogen. 1-Chloroethyl chloroformate (0.52 ml, 4.8 mmol) is added. The reaction medium is stirred for 16 h at 80° C. After concentrating to dryness, 5 ml of methanol are added and the resulting product is heated at 80° C. for 1 h 30. After the solvent has been evaporated off, a saturated aqueous NaHCO$_3$ solution is added and extraction is carried out with dichloromethane. The organic phase is dried over MgSO$_4$. The crude product obtained is chromatographed on silica gel, elution being carried out with a gradient of methanol/aqueous ammonia in dichloromethane ranging from 95/5/0.5 to 90/10/1 (dichloromethane/methanol/aqueous ammonia). 0.42 g of expected endo-3-[4-(4-methanesulfonylpiperazin-1-yl)phenoxy]-8-azabicyclo[32.1]octane is obtained.
[M+H$^+$]=366

4.4/endo-3-[4-(4-Methanesulfonylpiperazin-1-yl)phenoxy]-8-azabicyclo[3.2.1]-octane-8-carboxylic acid (trans-5-hydroxyadamantan-2-yl)amide endo-3-[4-(4-Methanesulfonylpiperazin-1-yl)phenoxy]-8-azabicyclo[3.2.1]-octane (0.21 g, 0.57 mmol) is placed in 6 ml of dichloromethane at 0° C. Triethylamine (0.18 ml, 1.26 mmol) and triphosgene (0.068 g, 0.23 mmol) are then added. After stirring for 3 h at ambient temperature, the resulting mixture is hydrolyzed and extraction is carried out with dichloromethane. The organic phase is dried over MgSO$_4$. The crude product is taken up in 10 ml of dichloromethane and 8 ml of anhydrous DMF. After the addition of 0.24 ml of triethylamine, trans-4-amino-adamantan-1-ol (0.115 g, 0.69 mmol) is added. The reaction medium is stirred at 55° C. for 16 h. After hydrolysis and extraction with ethyl acetate, the organic phase is washed with a saturated aqueous sodium chloride solution and dried over MgSO$_4$. The crude product obtained is chromatographed on silica gel, elution being carried out with a gradient of methanol in dichloromethane ranging from 0% to 10%. 0.09 g is obtained, which is triturated from an ethanol/ethyl acetate/diethyl ether mixture, to give 0.075 g of expected endo-3-[4-(4-methanesulfonylpiperazin-1-yl)phenoxy]-8-azabicyclo[3.2.1]octane-8-carboxylic acid (trans-5-hydroxyadamantan-2-yl)amide.
Melting point=252° C.; [M+H$^+$]=559
$^1$H NMR (400 MHz, DMSO-d6) δ ppm 6.9 (d, J=8.9 Hz, 2H), 6.8 (d, J=8.9 Hz, 2H), 5.8 (d, J=6.3 Hz, 1H), 4.6 (bt, J=4.3 Hz, 1H), 4.35 (s, 1H), 4.25 (bs, 2H), 3.7 (m, 1H), 3.25 (m, 4H), 3.1 (m, 4H), 2.9 (s, 3H), 2.1-1.55 (m, 19H), 1.3 (d, J=2.6 Hz, 2H).

EXAMPLE 5 exo-3-[5-(4-isopropoxyphenyl)pyridin-2-yloxy]-8-azabicyclo[3.2.1]octane-8-carboxylic acid (trans-5-carbamoyladamantan-2-yl)amide (Compound No. 9)

5.1/endo-3-Hydroxy-8-azabicyclo[3.2.1]octane-8-carboxylic acid tert-butyl ester Tropine (5 g, 35.4 mmol) is placed in 71 ml of dichloroethane at 0° C. under nitrogen. 1-Chloroethyl chloroformate (7.64 ml, 70.8 mmol) is added. The reaction medium is stirred for 2 h at 80° C. After concentrating to dryness, 40 ml of methanol are added and the mixture is heated to 80° C. for 1 h 15. After the solvent has been evaporated off, the crude product is dissolved in 35 ml of acetone and 35 ml of water. NaHCO$_3$ (11.9 g, 141 mmol) and t-butyl dicarbonate (23.2 g, 106 mmol) are added. The reaction medium is stirred for 16 h at ambient temperature. After the acetone has been evaporated off, the crude product is hydrolyzed and extracted with ethyl acetate. The organic phase is washed with a saturated aqueous sodium chloride solution and dried over MgSO$_4$. The crude product obtained is triturated from pentane. The insoluble material obtained is filter-dried and 6.05 g of expected endo-3-hydroxy-8-azabicyclo[3.2.1]octane-8-carboxylic acid tert-butyl ester are obtained.
M$^{+°}$=227

5.2/exo-3-(4-Nitrobenzoyloxy)-8-azabicyclo[3.2.1]octane-8-carboxylic acid tert-butyl ester endo-3-Hydroxy-8-azabicyclo[3.2.1]octane-8-carboxylic acid tert-butyl ester (0.5 g, 2.2 mmol) is placed in 7.5 ml of anhydrous THF in the presence of 4-nitro-benzoic acid (0.39 g, 2.38 mmol) and triphenylphosphine (0.692 g, 1.2 mmol). DIAD (0.51 ml, 2.64 mmol) is slowly added. The reaction medium is stirred at ambient temperature for 20 h. After concentrating to dryness, the crude product is chromatographed on silica gel, elution being carried out with a gradient of ethyl acetate in heptane ranging from 0% to 30%. 0.66 g of expected exo-3-(4-nitro-benzoyloxy)-8-azabicyclo[3.2.1]octane-8-carboxylic acid tert-butyl ester is obtained.
[M+H$^+$]=377

5.3/exo-3-Hydroxy-8-azabicyclo[3.2.1]octane-8-carboxylic acid tert-butyl ester exo-3-(4-Nitrobenzoyloxy)-8-azabicyclo[3.2.1]octane-8-carboxylic acid tert-butyl ester (0.66 g, 1.75 mmol) is placed in 6 ml of THF 0.9 ml of 4N aqueous sodium hydroxide is added. The reaction medium is stirred at ambient temperature for 4 h. 15 ml of water are then added and the mixture is extracted with dichloromethane. The organic phase is washed with a saturated aqueous sodium chloride solution and dried over MgSO$_4$. The crude product obtained is chromatographed on silica gel, elution being carried out with a gradient of methanol in dichloromethane ranging from 0% to 10%. 0.32 g of expected exo-3-hydroxy-8-azabicyclo[3.2.1]octane-8-carboxylic acid tert-butyl ester is obtained.
M$^{+°}$=227

5.4/exo-3-(5-Bromopyridin-2-yloxy)-8-azabicyclo[3.2.1]octane-8-carboxylic acid tert-butyl ester exo-3-Hydroxy-8-azabicyclo[3.2.1]octane-8-carboxylic acid tert-butyl ester (0.2 g, 0.88 mmol) is placed in 1.5 ml of NMP. 5-Bromo-2-pyridine (0.27 ml, 2.64 mmol) and potassium t-butoxide (0.20 g, 1.76 mmol) are added. The reaction medium is stirred for 10 min at ambient temperature and then for 15 min in a microwave at 80° C. After hydrolysis and extraction with ethyl acetate, the organic phase is washed with a saturated aqueous sodium chloride solution and dried over MgSO$_4$. The crude product obtained is chromatographed on silica gel, elution being carried out with a gradient of ethyl acetate in heptane ranging from 0% to 30%, 0.29 g of expected exo-3-(5-bromo-pyridin-2-yloxy)-8-azabicyclo[3.2.1]octane-8-carboxylic acid tert-butyl ester is obtained.
[M+H$^+$]=383

5.5/exo-3-[5-(4-Isopropoxyphenyl)pyridin-2-yloxy]-8-azabicyclo[3.2.1]octane-8-carboxylic acid tert-butyl ester exo-3-(5-Bromopyridin-2-yloxy)-8-azabicyclo[3.2.1]octane-8-carboxylic acid tert-butyl ester (0.5 g, 1.3 mmol) is placed in 13 ml of toluene in the presence of tetrakis(triphenylphosphine)palladium (0.15 g, 0.13 mmol), 4-isopropoxyphenyl-boronic acid (0.235 g, 1.3 mmol) and 1.63 ml of a 2M solution of potassium carbonate. The reaction medium is stirred at reflux for 16 h. After hydrolysis and extraction with ethyl acetate, the organic phase is washed with a saturated aqueous sodium chloride solution and dried over $MgSO_4$. The crude product obtained is chromatographed on silica gel, elution being carried out with a gradient of methanol in dichloromethane ranging from 0% to 10%. 0.33 g of expected exo-3-[5-(4-isopropoxyphenyl)pyridin-2-yloxy]-8-azabicyclo[3.2.1]octane-8-carboxylic acid tert-butyl ester is obtained.

$[M+H^+]=439$

5.6/exo-3-[5-(4-Isopropoxyphenyl)pyridin-2-yloxy]-8-azabicyclo[3.2.1]octane

According to a procedure identical to that described in 1.6, starting from exo-3-[5-(4-isopropoxyphenyl)pyridin-2-yloxy]-8-azabicyclo[3.2.1]octane-8-carboxylic acid tert-butyl ester (0.32 g, 0.73 mmol), the crude product obtained is concentrated to dryness, then hydrolyzed and extracted with diethyl ether. The aqueous phase is than basified to pH 10 with $K_2CO_3$, and extracted with dichloromethane. The organic phase is washed with a saturated aqueous sodium chloride solution, dried over $MgSO_4$ and concentrated to dryness. 0.28 g of expected exo-3-[5-(4-isopropoxy-phenyl)pyridin-2-yloxy]-8-azabicyclo[3.2.1]octane is obtained.

$[M+H^+]=339$

5.7/trans-4-Aminoadamantane-1-carboxylic acid 4-oxo-Adamantane-1-carboxylic acid (8 g, 41.2 mmol) is stirred under an $H_2$ atmosphere in the presence of palladium-on-carbon at 10% (0.5 g) in 160 ml of a 7N methanolic solution of ammonia, for 19 h. The solid in suspension is first of all filter-dried and washed with methanol, and is then taken up with 200 ml of water and the palladium-on-carbon is filtered off. The resulting product is concentrated to dryness, and taken up in a small amount of methanol, and then the white solid is filter-dried and subsequently dried over $P_2O_5$. 5.4 g of expected trans-4-aminoadamantane-1-carboxylic acid are obtained.

$[M+H^+]=196$

5.8/trans-4-tert-Butoxycarbonylaminoadamantane-1-carboxylic acid trans-4-Aminoadamantane-1-carboxylic acid (7.74 g, 39.6 mmol) is dissolved in 70 ml of a 1N aqueous sodium hydroxide solution and than 70 ml of dioxane are added. di-t-Butoxycarbonate (25.9 g, 118.9 mmol) is added. The reaction medium is stirred for 16 h at ambient temperature. After the dioxane has been evaporated off, the aqueous phase is extracted with dichloromethane. A 1N aqueous solution of HCl is then added until a pH of 4 is obtained. Extraction is carried out with dichloromethane. The organic phase is dried over $MgSO_4$ and concentrated to dryness, 10.5 g of expected trans-4-t-butoxycarbonylaminoadamantane-1-carboxylic acid are obtained.

$[M+H^+]=296$

5.9/trans-(5-Carbamoyladamantan-2-yl)carbamic acid tert-butyl ester trans-4-t-Butoxycarbonylaminoadamantane-1-carboxylic acid (5.8 g, 19.6 mmol) is placed in 100 ml of dichloromethane under nitrogen. Triethylamine (54.7 ml, 393 mmol) is added at 0° C., followed by ethyl chloroformate (3.75 ml, 39.3 mmol). Stirring is maintained at 0° C. for 2 h. Ammonium chloride (21 g, 393 mmol) is then added. After 30 minutes at 0° C., stirring is continued at ambient temperature for 4 h. After hydrolysis, and extraction with dichloromethane, the organic phase is dried over $MgSO_4$ and concentrated to dryness. The crude product obtained is chromatographed on silica gel, elution being carried out with a gradient of ethyl acetate/methanol in heptane ranging from 100/0/0 to 4/5/1. 4.0 g of trans-(5-carbamoyladamantan-2-yl)carbamic acid tert-butyl ester are obtained.

$[M+H^+]=295$

5.10/trans-(5-Carbamoyladamantan-2-yl)carbamic acid tert-butyl ester hydrochloride trans-(5-Carbamoyladamantan-2-yl)carbamic acid tert-butyl ester (4 g, 13.59 mmol) is placed in 51 ml of 4N HCl in dioxane, and the mixture is stirred at ambient temperature for 18 h. The white precipitate obtained is filter-dried and washed with diethyl ether. 3.2 g of trans-4-aminoadamantane-1-carboxylic acid amide hydrochloride are obtained.

$[M+H^+]=195$

5.11/exo-3-[5-(4-Isopropoxyphenyl)pyridin-2-yloxy]-8-azabicyclo[3.2.1]octane-8-carboxylic acid (trans-5-carbamoyladamantan-2-yl)amide exo-3-[5-(4-Isopropoxyphenyl)pyridin-2-yloxy]-8-azabicyclo[3.2.1]octane 0.28 g. 0.82 mmol) is placed in 8 ml of dichloromethane at 0° C. Triethylamine (0.23 ml, 1.64 mmol) and triphosgene (0.097 g, 0.33 mmol) are then added. After stirring for 3 h at ambient temperature, the reaction mixture is hydrolyzed and extracted with dichloromethane. The organic phase is washed with a saturated aqueous sodium chloride solution and dried over $MgSO_4$. The crude product is taken up in 3 ml of anhydrous DMF. trans-4-Aminoadamantane-1-carboxylic acid amide hydrochloride (0.276 g, 1.2 mmol) solubilized in 5 ml of DMF in the presence of diisopropylethylamine (0.42 ml, 2.39 mmol) is added. The reaction medium is stirred at 50° C. for 16 h. After hydrolysis and extraction with dichloromethane, the organic phase is washed with a saturated aqueous sodium chloride solution and dried over $MgSO_4$. The crude product obtained is chromatographed on silica gel, elution being carried out with a gradient of methanol in dichloromethane ranging from 0% to 10%. 0.095 g of expected exo-3-[5-(4-isopropoxyphenyl)pyridin-2-yloxy]-8-azabicyclo-[3.2.1]octane-8-carboxylic acid (trans-5-carbamoyladamantan-2-yl)amide is obtained.

Melting point=255° C.; $[M+H^+]=559$

$^1$H NMR (400 MHz, DMSO-d6) δ ppm: 8.4 (d, J=2.5 Hz, 1H), 7.9 (dd, J=8.6 and 2.5 Hz, 1H), 7.55 (d, J=8.8 Hz, 2H), 7.0 (d, J=8.8 Hz, 2H), 6.95 (s, 1H), 6.8 (d, J=8.5 Hz, 1H), 7.0-6.7 (bs, 1H), 5.95 (d, J=6.2 Hz, 1H), 5.5 (m, 1H), 4.65 (m, 1H), 4.4 (m, 2H), 3.75 (m, 1H), 2.1-1.3 (m, 27H).

EXAMPLE 6 exo-3-[6-(4-Methoxyphenyl)pyrimidin-2-yloxy]-8-azabicyclo[3.2.1]octane-8-carboxylic acid (trans-6-carbamoyladamantan-2-yl)amide (Compound No. 12)

6.1/exo-3-[6-(4-Methoxyphenyl)pyrimidin-2-yloxy]-8-methyl-8-azabicyclo-[3.2.1]octane Sodium hydride (0.25 g, 10.6 mmol) is placed in 15 ml of anhydrous NMP under nitrogen and a solution of pseudotropanol (1 g, 7.1 mmol) solubilized in 5 ml of anhydrous NMP is slowly added. The reaction medium is stirred for 1 h at 80° C. The solution is cooled to ambient temperature and 2-methanesulfonyl-5-(4-methoxy-phenyl)pyrimidine (2.81 g, 10.6 mmol) solubilized in 5 ml of anhydrous NMP is slowly added. The reaction medium is stirred for 1 h 30 at ambient temperature and then for 1 h at 80° C. After hydrolysis and extraction with ethyl acetate, the organic phase is washed with a saturated aqueous sodium chloride solution and dried over MgSO$_4$. The crude product obtained is chromatographed on silica gel, elution being carried out with a gradient of methanol/aqueous ammonia in dichloromethane ranging from 90/10/1 to 70/30/3 (dichloromethane/methanol/aqueous ammonia). 1.3 g of expected exo-3-[5-(4-methoxyphenyl)pyrimidin-2-yloxy]-8-methyl-8-azabicyclo[3.2.1]octane are obtained.

[M+H$^+$]=326

6.2/exo-3-[5-(4-Methoxyphenyl)pyrimidin-2-yloxy]-8-azabicyclo[3.2.1]octane exo-3-[5-(4-Methoxyphenyl)pyrimidin-2-yloxy]-8-methyl-8-azabicyclo[3.2.1]-octane (0.5 g, 1.54 mmol) is placed in 3 ml of dichloroethane at 0° C. under nitrogen, 1-Chloroethyl choroformate (0.33 ml, 3.1 mmol) is added. The reaction medium is stirred for 18 h at 80° C. After concentrating to dryness, 3 ml of methanol are added and the mixture is heated to 80° C. for 2 h. After the solvent has been evaporated off, hydrolysis is carried out with a saturated aqueous NaHCO$_3$ solution, extraction is carried out with ethyl acetate, and the organic phase is dried over MgSO$_4$. The crude product obtained is chromatographed on silica gel, elution being carried out with a gradient of methanol/aqueous ammonia in dichloromethane ranging from 100/0/0 to 90/10/1 (dichloromethane/methanol/aqueous ammonia). 0.27 g of expected exo-3-[5-(4-methoxyphenyl)pyrimidin-2-yloxy]-8-methyl-8-azabicyclo[3.2.1]octane is obtained.

[M+H$^+$]=312

6.3/exo-3-[5-(4-Methoxyphenyl)pyrimidin-2-yloxy]-8-azabicyclo[3.2.1]octane-8-carboxylic acid (trans-5-carbamoyladamantan-2-yl)amide exo-3-[5-(4-Methoxyphenyl)pyrimidin-2-yloxy]-8-methyl-8-azabicyclo[3.2.1]-octane (0.21 g, 0.66 mmol) is placed in 22 ml of a 50/50 mixture of dichloromethane/saturated aqueous NaHCO$_3$ solution at 0° C. A 20% solution of phosgene in toluene (0.52 ml, 0.99 mmol) is added. After stirring for 2 h, the aqueous phase is extracted with dichloromethane. The organic phase is dried over MgSO$_4$. The crude product obtained is placed in 7 ml of anhydrous DMF under nitrogen. Triethylamine (0.23 ml, 1.65 mmol) is added, followed by trans-4-aminoadamantane-1-carboxylic acid amide hydrochloride (0.128 g, 0.66 mmol). The reaction medium is heated at 50° C. for 16 h. After hydrolysis with a saturated aqueous NaHCO$_3$ solution and extraction with ethyl acetate, the organic phase is washed with a saturated aqueous sodium chloride solution and dried over MgSO$_4$. The crude product obtained is chromatographed on silica gel, elution being carried out with a gradient of acetone/methanol in dichloromethane ranging from 100/0/0 to 70/25/5 (dichloromethane/acetone/methanol). After trituration from a mixture of ethyl acetate and diethyl ether, 0.138 g of exo-3-[5-(4-methoxyphenyl)pyrimidin-2-yloxy]-8-azabicyclo[3.2.1]octane-8-carboxylic acid (trans-5-carbamoyltransadamantan-2-yl)amide is obtained.

Melting point=238° C.; [M+H$^+$]=532.

$^1$H NMR (400 MHz, DMSO-d6) δ ppm: 8.9 (s, 2H), 7.7 (d, J=8.9 Hz, 2H), 7.1 (d, J=8.8 Hz, 2H), 7.0 (bs, 1H), 6.7 (bs, 1H), 6.0 (d, J=6.2 Hz, 1H), 5.45 (m, J=5.5 Hz, 1H), 4.4 (m, 2H), 3.8 (s, 3H), 3.75 (m, 1H), 2.1 (m, 2H), 2.05-1.65 (m, 17H), 1.4 (m, 2H).

EXAMPLE 7 endo-3-Hydroxy-3-[4-(4-methanesulfonylpiperazin-1-yl)phenoxymethyl]-8-aza-bicyclo[3.2.1]octane-8-carboxylic acid (trans-5-hydroxyadamantan-2-yl) amide (Compound No 15)

7.1/8-Benzyl-spiro[8-azabicyclo[3.2.1]octane-3,2'-oxirane]

Trimethyl sulfoxonium iodide (3.07 g, 13.9 mmol) is placed in 18 ml of DMSO under nitrogen in the presence of sodium hydride dispersed at 60% in oil (0.56 g, 13.9 mmol). After stirring for 30 min at ambient temperature, 8-benzyl-8-aza-bicyclo[3.2.1]octan-3-one (2.0 g, 9.3 mmol) solubilized in 3 ml of DMSO is slowly added. The reaction medium is kept stirring for 4 h and then kept without stirring for 60 h, After hydrolysis, and extraction with ethyl acetate, the organic phase is washed with a saturated aqueous sodium chloride solution and dried over MgSO$_4$. 2.04 g of 8-benzyl-spiro[8-azabicyclo[3.2.1]octane-3,2'-oxirane], subsequently used as it is, are obtained.

[M+H$^+$]=230

7.2/Methanesulfonic acid 4-(4-methanesulfonylpiperazin-1-yl)phenyl ester 4-piperazin-1-ylphenol (2.0 g, 11.2 mmol) is placed in 22 ml of pyridine at 0° C. Mesyl chloride (1.9 ml, 24.7 mmol) is slowly added. Stirring is maintained for 2 h at 0° C. and then for 2 h at ambient temperature. 80 ml of water are then added. The precipitate obtained is filter-dried and washed with water, than dried over P$_2$O$_5$. 3.2 g of expected methanesulfonic acid 4-(4-methanesulfonylpiperazin-1-yl)phenyl ester are obtained.

[M+H$^+$]=335

7.3/4-(4-Methanesulfonylpiperazin-1-yl)phenol

Methanesulfonic acid 4-(4-methanesulfonylpiperazin-1-yl)phenyl ester (3.2 g, 9.5 mmol) is placed in 29 ml of a 1N aqueous solution of sodium hydroxide. The reaction medium is stirred at reflux for 48 h. Acetic acid is added at ambient temperature to pH 4. The precipitate formed is filter-dried and washed with water and then dried over P$_2$O$_5$. 2.6 g of expected 4-(4-methanesulfonylpiperazin-1-yl)phenol are obtained.

[M+H$^+$]=257

7.4/8-Benzyl-3-[4-(4-methanesulfonylpiperazin-1-yl)phenoxymethyl]-8-aza-bicyclo[3.2.1]octan-3-endo-ol 4-(4-Methanesulfonylpiperazin-1-yl)phenol (1.5 g, 5.7 mmol) is placed in 22 ml of anhydrous DMF under nitrogen. Sodium hydride dispersed at 60% in oil (0.21 g, 5.3 mmol) is slowly added. After stirring for 1 h at ambient temperature, 8-benzyl-spiro[8-azabicyclo[3.2.1]octane-3,2'-oxirane] (1.1 g, 4.8 mmol) solubilized in 2 ml of anhydrous DMF is added. The reaction medium is stirred at 115° C. for 5 h. 8-Benzyl-spiro[8-azabicyclo[3.2.1]octane-3,2'-oxirane] (0.42 g, 1.6 mmol) and sodium hydride dispersed at 60% in oil (0.04 g, 1 mmol) are then again added. Stirring is maintained at 115° C. for 18 h. After hydrolysis with a saturated aqueous NaHCO$_3$ solution, and extraction with ethyl acetate and with dichloromethane, the organic phase is washed with a saturated aqueous sodium chloride solution and dried over MgSO$_4$. Ethyl acetate is added and the insoluble material formed is filter-dried. The filtrate is concentrated and chromatographed on silica gel, elution being carried out with a gradient of methanol in dichloromethane ranging from 0% to 10%. 0.145 g of expected 8-benzyl-3-[4-(4-methanesulfonylpiperazin-1-yl)phenoxymethyl]-8-aza-bicyclo[3.2.1]octan-3-endo-ol is obtained.

[M+H$^+$]=486

7.5/3-[4-(4-Methanesulfonylpiperazin-1-yl)phenoxymethyl]-8-azabicyclo[3.2.1]-octan-3-endo-ol 8-Benzyl-3-[4-(4-methanesulfonylpiperazin-1-yl)phenoxymethyl]-8-azabicyclo-[3.2.1]octan-3-endo-ol (1.7 g, 3.0 mmol) is placed in 60 ml of methanol. Ammonium formate (1.87 g, 29.7 mmol) and palladium-on-carbon 10%, ~50% in water (0.4 g), are added. The reaction medium is refluxed for 1 h 30. After the catalyst has been filtered off, the filtrate is concentrated. The crude product obtained is chromatographed on silica gel, elution being carried out with a gradient of methanol/-aqueous ammonia in dichloromethane ranging from 100/0/0 to 87/13/1.3 (dichloromethane/methanol/aqueous ammonia). 0.19 g of expected 3-[4-(4-methane-sulfonylpiperazin-1-yl)phenoxymethyl]-8-azabicyclo[3.2.1]octan-3-endo-ol is obtained.

[M+H$^+$]=396

7.6/endo-3-Hydroxy-3-[4-(4-methanesulfonylpiperazin-1-yl)phenoxymethyl]-8-azabicyclo[3.2.1]octane-8-carboxylic acid (trans-6-hydroxyadamantan-2-yl)-amide 3-[4-(4-Methanesulfonylpiperazin-1-yl)phenoxymethyl]-8-azabicyclo[3.2.1]-octan-3-endo-ol (0.6 g, 1.5 mmol) is placed in 51 ml of a 50/50 mixture of dichloromethane/saturated aqueous NaHCO$_3$ solution at 0° C. A 20% solution of phosgene in toluene (1.2 ml, 2.28 mmol) is added. After stirring for 2 h, a 20% solution of phosgene in toluene (1 ml) is again added and stirring is maintained for 30 min at 0° C. After extraction of the aqueous phase with dichloromethane, the organic phase is dried over MgSO$_4$. The crude product obtained is placed in 7 ml of anhydrous DMF under nitrogen. Triethylamine (0.21 ml, 1.48 mmol) is added, followed by trans-4-aminoadamantan-1-ol (0.14 g, 0.82 mmol) dissolved in 1.5 ml of anhydrous DMF. The reaction medium is heated at 60° C. for 16 h. After hydrolysis with a saturated aqueous NaHCO$_3$ solution, and extraction with ethyl acetate, the organic phase is washed with a saturated aqueous sodium chloride solution. After concentrating to dryness, the crude product obtained is taken up with acetonitrile and with methanol under hot conditions. The insoluble material is filtered off and the filtrate is chromatographed, after concentration, on silica gel, elution being carried out with a gradient of methanol in dichloromethane ranging from 0% to 10%. 0.30 g of expected endo-3-hydroxy-3-[4-(4-methanesulfonylpiperazin-1-yl)phenoxymethyl]-8-azabicyclo[3.2.1]octane-8-carboxylic acid (trans-5-hydroxyadamantan-2-yl)amide is obtained.

Melting point=249° C.; [M+H$^+$]=589

$^1$H NMR (400 MHz, DMSO-d6) δ ppm: 6.9 (d, J=9 Hz, 2H), 6.75 (d, J=9 Hz, 2H), 5.7 (d, J=6 Hz, 1H), 4.5 (s, 1H), 4.35 (s, 1H), 4.2 (m, 2H), 3.65 (m, 1H), 3.4 (s, 2H), 3.2 (m, 4H), 3.1 (m, 4H), 2.9 (s, 3H), 2.2-1.2 (m, 21H)

EXAMPLE 8 endo-3-[4-(4-Methanesulfonylpiperazin-1-yl)phenoxymethyl]-8-azabicyclo-[3.2.1]octane-8-carboxylic acid (trans-6-hydroxyadamantan-2-yl)amide (Compound No. 17)

8.1/8-Azabicyclo[3.2.1]oct-2-ene-3,8-dicarboxylic acid 8-tert-butyl ester

3-Trifluoromethanesulfonyloxy-8-azabicyclo[3.2.1]oct-2-ene-8-carboxylic acid tert-butyl ester (2.0 g, 5.6 mmol), hexacarbonylmolybdenum (0.74 g, 2.8 mmol), palladium diacetate (0.13 g, 0.56 mmol), 1,1'-bis(diphenylphosphino) ferrocene (0.31 g, 0.56 mmol), 4-dimethylaminopyridine (1.37 g, 11.2 mmol) and diisopropyl-ethylamine (2.24 ml, 12.9 mmol) are placed in 2.0 ml of water and 12 ml of dioxane in a microwave reaction vessel. The medium is microwave-heated at 150° C. for 10 min. The crude product is taken up with water and with dichloromethane. The organic phase is extracted with a saturated aqueous NaHCO$_3$ solution. The aqueous phase is acidified with KHSO$_4$ and then extracted with ethyl acetate. The organic phase is washed with water and then with a saturated aqueous sodium chloride solution and dried over MgSO$_4$. After concentrating to dryness, 2.7 g of expected 8-aza-bicyclo[3.2.1]oct-2-ene-3,8-dicarboxylic acid 8-tert-butyl ester are obtained.

[M+H$^+$]=253

8.2/endo-8-Azabicyclo[3.2.1]octane-3,8-dicarboxylic acid 8-tert-butyl ester 8-Azabicyclo[3.2.1]oct-2-ene-3,8-dicarboxylic acid 8-tert-butyl ester (2.7 g, 10.7 mmol) is placed in 71 ml of methanol. Platinum oxide (0.24 g, 1.07 mmol) is then added under nitrogen. The reaction medium is placed under 50 psi of hydrogen at 20° C. After stirring for 6 h, the catalyst is filtered off and rinsed with methanol. The filtrate is concentrated to dryness and chromatographed on silica gel, elution being carried out with a gradient of ethyl acetate/methanol in heptane ranging from 100/0/0 to 5/4.5/0.5 (heptane/ethyl acetate/methanol). 1.12 g of expected endo-8-aza-bicyclo[3.2.1]octane-3,8-dicarboxylic acid 8-tert-butyl ester and 0.32 g of exo-8-aza-bicyclo[3.2.1]octane-3,8-dicarboxylic acid 8-tert-butyl ester are obtained. [M+H$^+$] (-tBu)=200

8.3/endo-3-Hydroxymethyl-8-azabicyclo[3.2.1]octane-8-carboxylic acid tert-butyl ester endo-8-Azabicyclo[3.2.1]octane-3,8-dicarboxylic acid 8-tert-butyl ester (1.12 g. 4.4 mmol) is placed in 22 ml of anhydrous THF under nitrogen at 0° C. Borane complexed with THF, 1N in THF (17.5 ml, 17.5 mmol), is slowly added. At the end of the addition, the reaction medium is stirred at ambient temperature for 1 h 30. Hydrolysis is carried out at 0° C. by slowly adding water. Ethyl acetate and then KHSO₄ are subsequently added. After extraction with ethyl acetate, the organic phase is washed with a saturated aqueous NaHCO₃ solution, then with water and, finally, with a saturated aqueous sodium chloride solution, and then dried over MgSO₄. After concentrating to dryness, 1.04 g of expected endo-3-hydroxymethyl-8-azabicyclo[3.2.1]octane-8-carboxylic acid tert-butyl ester are obtained.

[M+H$^+$]=232

8.4/endo-3-(4-Bromophenoxymethyl)-8-azabicyclo [3.2.1]octane-8-carboxylic acid tert-butyl ester Sodium hydride (0.16 g, 6.5 mmol) is placed in 5 ml of anhydrous DMF under nitrogen. Tropine (1.04 g, 4.3 mmol) solubilized in 10 ml of anhydrous DMF is slowly added. The reaction medium is heated at 65° C. for 1 h and then 4-fluorobenzene (1.13 g, 6.5 mmol) placed in 5 ml of anhydrous DMF is slowly added. After stirring at 65° C. for 5 h, sodium hydride (0.05 g, 2.1 mmol) is again added and heating is maintained at 65° C. for 3 h. The reaction medium is hydrolyzed with a water/ice mixture. Extraction is carried out with ethyl acetate. The organic phase is washed with water and then with a saturated aqueous sodium chloride solution and dried over MgSO₄. The crude product obtained is chromatographed on silica gel, elution being carried out with a gradient of ethyl acetate/methanol in heptane ranging from 100/0/0 to 5/4.5/0.5 (heptane/ethyl acetate/methanol). 1.05 g of expected endo-3-(4-bromophenoxymethyl)-8-azabicyclo [3.2.1]octane-8-carboxylic acid tert-butyl ester are obtained.

[M+H$^+$]=296

8.5/endo-3-[4-(4-Methanesulfonylpiperazin-1-yl) phenoxymethyl]-8-azabicyclo-[3.2.1]octane-8-carboxylic acid tert-butyl ester endo-3-(4-Bromophenoxymethyl)-8-azabicyclo[3.2.1]octane-8-carboxylic acid tert-butyl ester (1.05 g, 2.65 mmol), 1-methanesulfonylpiperazine (0.52 g, 3.2 mmol), the 2'-(dimethylamino)-2-biphenylyl-palladium(II) chloride dinorbornylphosphine complex catalyst (0.22 g, 0.4 mmol) and potassium phosphate (1.41 g, 6.6 mmol) are placed in 13 ml of DME under nitrogen. The reaction medium is stirred at 90° C. for 4 h 30. 1-Methanesulfonylpiperazine (0.13 g, 0.8 mmol) and the 2'-(dimethylamino)-2-biphenylyl-palladium (II) chloride dinorbornylphosphine complex catalyst (0.075 g, 0.13 mmol) are then added. Stirring is maintained at 90° C. for 16 h. After hydrolysis, and extraction with dichloromethane, the organic phase is washed with water and then with a saturated aqueous sodium chloride solution and dried over MgSO₄. The crude product obtained is chromatographed on silica gel, elution being carried out with a gradient of methanol in dichloromethane ranging from 0% to 2.5%. 0.56 g of expected endo-3-[4-(4-methanesulfonylpiperazin-1-yl)phenoxymethyl]-8-azabicyclo-[3.2.1]octane-8-carboxylic acid tert-butyl ester is obtained.

[M+H$^+$]=480

8.6/endo-3-[4-(4-Methanesulfonylpiperazin-1-yl) phenoxymethyl]-8-azabicyclo-[3.2.1]octane endo-3-[4-(4-Methanesulfonylpiperazin-1-yl)phenoxymethyl]-8-azabicyclo-[3.2.1]octane-8-carboxylic acid tert-butyl ester (0.56 g, 1.17 mmol) is solubilized in 2 ml of dichloromethane. 4N HCl in dioxane (4.3 ml, 17.5 mmol) is then added. After stirring for 3 h 30 at ambient temperature, the reaction medium is concentrated, and taken up with water and with a 1N aqueous solution of sodium hydroxide until pH 10 is obtained. After extraction with dichloromethane, and washing with water and then with a saturated aqueous sodium chloride solution, the organic phase is dried over MgSO₄ and then concentrated to dryness. 0.42 g of expected endo-3-[4-(4-methane-sulfonylpiperazin-1-yl)phenoxymethyl]-8-azabicyclo[3.2.1]octane is obtained, which is subsequently used as it is.

[M+H$^+$]=380

8.7/endo-3-[4-(4-Methanesulfonylpiperazin-1-yl)-phenoxymethyl]-8-azabicyclo-[3.2.1]octane-8-carboxylic acid (trans-5-hydroxyadamantan-2-yl)amide endo-3-[4-(4-Methanesulfonylpiperazin-1-yl)phenoxymethyl]-8-azabicyclo-[3.2.1]octane (0.42 g, 1.1 mmol) is placed in 11 ml of dichloromethane at 0° C. under nitrogen. Triethylamine (0.31 ml, 2.19 mmol) and triphosgene (0.13 g, 0.44 mmol) are then added. After stirring for 2 h at ambient temperature, the reaction mixture is hydrolyzed and extraction is carried out with dichloromethane. The organic phase is washed with water and then with a saturated aqueous sodium chloride solution and dried over MgSO₄. 0.48 g of crude product is obtained. 0.24 g of this crude product is placed in 8 ml of anhydrous DMF and it is run into a solution of trans-4-aminoadamantan-1-ol (0.104 g, 0.62 mmol) in 1.5 ml of DMF and 0.11 ml of triethylamine. The reaction medium is stirred at 50° C. for 16 h. After hydrolysis, and extraction with ethyl acetate, the organic phase is washed with water and then with a saturated aqueous sodium chloride solution and dried over MgSO₄. After hot filtration in a methanol/acetonitrile mixture, the mother liquors are concentrated and the crude product obtained is chromatographed on silica gel, elution being carried out with a gradient of methanol in dichloromethane ranging from 0% to 10%. 0.167 g of expected compound is obtained, which is triturated from ethyl acetate and then filter-dried and dried, to give 0.120 g of expected endo-3-[4-(4-methanesulfonylpiperazin-1-yl)phenoxy]-8-azabicyclo[3.2.1]octane-8-carboxylic acid (trans-5-hydroxyadamantan-2-yl)amide.

Melting point=227° C.; [M+H$^+$]=573

$^1$H NMR (400 MHz, DMSO-d6) δ ppm: 6.9 (m, 4H), 5.75 (d, J=6.3 Hz, 1H), 4.35 (s, 1H), 4.25 (m, 2H), 3.9 (d, J=7.7 Hz, 2H), 3.65 (m, 1H), 3.25 (m, 4H), 3.1 (m, 4H), 2.95 (s, 3H), 2.1 (m, 2H), 2.05-1.8 (m, 8H), 1.7-1.55 (m, 8H), 1.4 (m, 2H), 1.3 (m, 2H).

EXAMPLE 9 endo-3-[5-(4-tert-Butylpiperazin-1-yl)pyridin-2-yloxymethyl]-8-azabicyclo-[3.2.1]octane-8-carboxylic acid (trans-6-hydroxyadamantan-2-yl)amide (Compound No. 21)

9.1/1-tert-Butyl-4-(6-fluoropyridin-3-yl)piperazine 1-tert-Butylpiperazine (1.61 g, 11.4 mmol) is placed in 35 ml of toluene under nitrogen, 5-Bromo-2-fluoropyridine (2 g, 11.4 mmol), sodium t-butoxide (1.6 g, 17 mmol), tris(dibenzylideneacetone)dipalladium (0.52 g, 0.57 mmol), and S-Phos (0.93 g, 17 mmol) are then added. The reaction medium is heated at 80° C. for 18 h. After hydrolysis, and extraction with ethyl acetate, the organic phase is washed with water and then with a saturated aqueous sodium chloride solution. After drying over MgSO$_4$, and concentrating to dryness, the crude product obtained is chromatographed on silica gel, elution being carried out with a gradient of methanol in dichloromethane ranging from 0% to 5%. 1.92 g of 1-tert-butyl-4-(6-fluoropyridin-3-yl)piperazine are obtained.

[M+H$^+$]=238

9.2/endo-3-[4-(4-tert-Butylpiperazin-1-yl)phenoxymethyl]-8-azabicyclo[3.2.1]-octane-8-carboxylic acid tert-butyl ester Sodium hydride (0.078 g, 3.11 mmol) is placed in 6.9 ml of anhydrous DMF under nitrogen. endo-3-Hydroxymethyl-8-azabicyclo[3.2.1]octane-8-carboxylic acid tert-butyl ester (0.5 g, 2.07 mmol) dissolved in 9 ml of anhydrous DMF is added to the sodium hydride at 95% (0.078 g, 3.11 mmol) under nitrogen. The reaction medium is heated at 65° C. for 1 h. 1-tert-Butyl-4-(6-fluoropyridin-3-yl)piperazine (0.58 g. 2.5 mmol) dissolved in 4 ml of anhydrous DMF is then added. The reaction medium is heated at 65° C. for 1 h 30. Sodium hydride at 95% (0.078 g, 3.11 mmol) is then again added. The reaction medium is heated at 80° C. for 1 h 30 and is then poured onto ice. After extraction with ethyl acetate, the organic phase is washed with a saturated aqueous sodium chloride solution. After drying over MgSO$_4$, and concentrating to dryness, the crude product obtained is chromatographed on silica gel, elution being carried out with a gradient of methanol in dichloromethane ranging from 0% to 5%. 2.86 g of a mixture are obtained, which mixture is taken up in 25 ml of dichloromethane, and washed with water and then with a saturated aqueous sodium chloride solution. After drying over MgSO$_4$, and concentrating to dryness, 1.2 g of endo-3-[4-(4-tert-butylpiperazin-1-yl)phenoxymethyl]-8-azabicyclo[3.2.1]-octane-8-carboxylic acid tert-butyl ester are obtained.

[M+H$^+$]=459

9.3/endo-3-[4-(4-tert-Butylpiperazin-1-yl)phenoxymethyl]-8-azabicyclo-[3.2.1]octane endo-3-[4-(4-bad-Butylpiperazin-1-yl)phenoxymethyl]-8-azabicyclo[3.2.1]-octane-8-carboxylic acid tert-butyl ester (1.2 g, 1.8 mmol) is placed in 3 ml of dichloromethane. The reaction medium is cooled to 0° C. and then 4N HCl in dioxane (6.8 ml, 27.5 mmol) is slowly added. After stirring for 4 h at ambient temperature and concentrating to dryness, the crude product obtained is hydrolyzed and washed with diethyl ether. The aqueous solution is then basified with potassium carbonate to pH>10. After extraction with dichloromethane, the organic phase is washed with a saturated aqueous sodium chloride solution. After drying over MgSO$_4$, and concentrating to dryness, the crude product obtained is chromatographed on silica gel, elution being carried out with a mixture of methanol/aqueous ammonia in dichloromethane ranging from 100/0/0 to 90/10/1 (dichloromethane/methanol/-aqueous ammonia). 0.47 g of expected endo-3-[4-(4-tert-butylpiperazin-1-yl)-phenoxymethyl]-8-azabicyclo[3.2.1]octane is obtained.

[M+H$^+$]=359

9.4/endo-3-[4-(4-tert-Butylpiperazin-1-yl)phenoxymethyl]-8-azabicyclo[3.2.1]-octane-8-carboxylic acid (trans-5-hydroxyadamantan-2-yl)amide endo-3-[4-(4-tert-Butylpiperazin-1-yl)phenoxymethyl]-8-azabicyclo[3.2.1]-octane (0.72 g, 2 mmol) is placed in 20 ml of dichloromethane under nitrogen. Triethylamine (0.56 ml, 4 mmol) is added. The reaction medium is placed at 0° C. and triphosgene (0.24 g, 0.8 mmol) is added. The mixture is stirred at ambient temperature for 2 h. After hydrolysis, and extraction with dichloromethane, the organic phase is washed with water and then with a saturated aqueous sodium chloride solution, dried over MgSO$_4$ and concentrated to dryness. 0.97 g of crude product is obtained. 0.28 g of this crude product is placed in 6 ml of anhydrous DMF under nitrogen. Triethylamine (0.21 ml, 1.5 mmol) is added, followed by trans-4-aminoadamantan-1-ol hydrochloride (0.145 g, 0.7 mmol). The reaction medium is stirred at 50° C. for 18 h. After filtration of the reaction medium, the filtrate is hydrolyzed, and extracted with dichloromethane. After washing of the organic phase with water and than with a saturated aqueous sodium chloride solution, drying over MgSO$_4$ and concentrating to dryness, the crude product obtained is chromatographed on silica gel, elution being carried out with a mixture of methanol/aqueous ammonia in dichloromethane ranging from 100/0/0 to 95/5/0.5 (dichloromethane/methanol/aqueous ammonia). 0.04 g of endo-3-[4-(4-tert-butylpiperazin-1-yl)phenoxymethyl]-8-azabicyclo[3.2.1]octane-8-carboxylic acid (trans-5-hydroxyadamantan-2-yl)amide is obtained.

Melting point=211° C. [M+H$^+$]=552

$^1$H NMR (400 MHz, DMSO-d6) δ ppm: 7.73 (d, J=3.1 Hz, 1H), 7.41 (dd, J=9.1 Hz and 3 Hz, 1H), 6.69 (d, J=9 Hz, 1H), 5.74 (d, J=6.4 Hz, 1H), 4.33 (s, 1H), 4.27-4.18 (m, 4H), 3.65 (m, 1H), 3.02 (m, 4H), 2.64 (m, 4H), 2.15-1.81 (m, 9H), 1.71-1.55 (m, 7H), 1.38 (m, 2H), 1.28 (m, 2H), 1.05 (s, 9H).

EXAMPLE 10

3-[4-(4-Methanesulfonylpiperazin-1-yl)pyridyl]-3,8-diazabicyclo[3.2.1]octane-8-carboxylic acid (trans-5-hydroxyadamantan-2-yl)amide (Compound No. 25)

10.1/3-(4-Bromopyridyl)-3,8-diazabicyclo[3.2.1]octane-8-carboxylic acid tert-butyl ester 3,8-Diazabicyclo[3.2.1]octane-8-carboxylic acid tert-butyl ester (0.4 g, 1.9 mmol), 2,5-dibromopyridine (0.58 g, 2.45 mmol), tris(dibenzylideneacetone)-dipalladium (0.07 g, 0.08 mmol), Xantphos (0.131 g, 0.23 mmol) and sodium t-butoxide (0.27 g, 2.8 mmol) are placed in 19 ml of toluene under nitrogen. The reaction medium is stirred at reflux for 4 h. After hydrolysis, and extraction with ethyl acetate, the aqueous phase is washed with a saturated aqueous sodium chloride solution and dried over MgSO$_4$. The crude product obtained is chromatographed on silica gel, elution being carried out with a gradient of ethyl acetate in heptane ranging from 0% to 30%. 0.54 g of expected 3-(4-bromopyridyl)-3,8-diazabicyclo-[3.2.1]octane-8-carboxylic acid tert-butyl ester is obtained.

[M+H$^+$]=368

10.2/3-[4-(4-Methanesulfonylpiperazin-1-yl)pyridyl]-3,8-diazabicyclo[3.2.1]-octane-8-carboxylic acid tert-butyl ester 3-(4-Bromophenyl)-3,8-diazabicyclo[3.2.1]octane-8-carboxylic acid tert-butyl ester (0.64 g, 1.7 mmol), 1-methanesulfonylpiperazine (0.43 g, 2.6 mmol), tris-(dibenzylideneacetone)dipalladium (0.069 g, 0.07 mmol), S-Phos (0.11 g, 0.28 mmol), and sodium t-butoxide (0.25 g, 2.6 mmol) are placed in 10 ml of toluene under nitrogen. The reaction medium is stirred at reflux for 1 h 30. After hydrolysis with a saturated aqueous NaHCO$_3$ solution, and extraction with ethyl acetate, the organic phase is washed with a saturated aqueous sodium chloride solution and dried over MgSO$_4$. The crude product obtained is chromatographed on silica gel, elution being carried out with a gradient of methanol/ethyl acetate in dichloromethane ranging from 100/0/0 to 7/2.5/0.5 (dichloromethane/ethyl acetate/methanol). 0.75 g of expected 3-[4-(4-methanesulfonylpiperazin-1-yl)phenyl]-3,8-diazabicyclo[3.2.1]-octane-8-carboxylic acid tert-butyl ester is obtained.

[M+H$^+$]=452

10.3/3-[4-(4-Methanesulfonylpiperazin-1-yl)phenyl]-3,8-diazabicyclo[3.2.1]-octane 3-[4-(4-Methanesulfonylpiperazin-1-yl)pyridyl]-3,8-diazabicyclo[3.2.1]octane-8-carboxylic acid tert-butyl ester (0.75 g, 1.66 mmol) is solubilized in 16 ml of dioxane. 4N HCl in dioxane (4.3 ml, 17.5 mmol) is then added, followed by approximately 3 ml of methanol. After stirring for 16 h at ambient temperature, the reaction medium is concentrated, and taken up with water. After extraction with diethyl ether, the pH of the aqueous phase is brought to pH 10 with K$_2$CO$_3$ in the presence of dichloromethane. After extraction with dichloromethane, the organic phase is washed with a saturated aqueous sodium chloride solution, and dried over MgSO$_4$, and then concentrated to dryness. 0.59 g of expected 3-[4-(4-methane-sulfonylpiperazin-1-yl)pyridyl]-3,8-diazabicyclo[3.2.1]octane is obtained, which is subsequently used as it is.

[M+H$^+$]=352

10.4/3-[4-(4-Methanesulfonylpiperazin-1-yl)pyridyl]-3,8-diazabicyclo[3.2.1]octane-8-carboxylic acid (trans-6-hydroxyadamantan-2-yl)amide 3-[4-(4-Methanesulfonylpiperazin-1-yl)pyridyl]-3,8-diazabicyclo[3.2.1]octane (0.46 g, 1.32 mmol) is placed in 13 ml of dichloromethane at 0° C. under nitrogen. Triethylamine (0.37 ml, 2.64 mmol) and triphosgene (0.157 g, 0.53 mmol) are then added. After stirring for 3 h at ambient temperature, the reaction mixture is hydrolyzed with a water/ice mixture and extraction is carried out with dichloromethane. The organic phase is washed with a saturated aqueous sodium chloride solution and dried over MgSO$_4$. 0.57 g of crude product is obtained. 0.20 g of this crude product is placed in 5 ml of anhydrous DMF. Triethylamine (0.17 ml, 1.21 mmol) is added, followed by trans-4-aminoadamantan-1-ol hydrochloride (0.12 g, 0.58 mmol). The reaction medium is stirred at 50° C. for 16 h. After hydrolysis, and extraction with dichloromethane, the organic phase is washed with water and then with a saturated aqueous sodium chloride solution and dried over MgSO$_4$. The crude product obtained is chromatographed on silica gel, elution being carried out with a gradient of methanol in dichloromethane ranging from 0% to 10%. 0.13 g of expected compound is obtained, which is triturated from diisopropyl ether and then filter-dried and dried, to give 0.84 g of expected 3-[4-(4-methanesulfonylpiperazin-1-yl) pyridyl]-3,8-diazabicyclo[3.2.1]octane-8-carboxylic acid (trans-5-hydroxyadamantan-2-yl)-amide.

Melting point=243° C.; [M+H$^+$]=545

$^1$H NMR (400 MHz, DMSO-d6) δ ppm: 7.9 (d, J=2.8 Hz, 1H); 7.5 (dd, J=9.2 and 2.8 Hz, 1H), 6.7 (d, J=9.2 Hz, 1H), 6.1 (d, J=6.2 Hz, 1H), 4.4 (s, 2H), 4.3 (s, 1H), 3.85 (d, J=11.7 Hz, 2H), 3.7 (m, 1H), 3.2 (m, 4H), 3.1 (m, 4H), 2.95 (s, 3H), 2.85 (m, 2H), 2.0-1.3 (m, 17H).

The table which follows illustrates the chemical structures and the physical properties of some examples of compounds according to the invention. In this table:

Me, Et, n-Pr, i-Pr, n-Bu and i-Bu are, respectively, methyl, ethyl, n-propyl, isopropyl, n-butyl and isobutyl groups, and Ph and Bn are, respectively, phenyl and benzyl groups, the Mp column indicates the melting point, in ° C., of the compound, and the proton magnetic resonance ($^1$H NMR) spectra, as described below, are recorded at 400 MHz in DMSO-d6, using the DMSO-d5 peak as reference. The chemical shifts δ are expressed in parts per million (ppm). The signals observed are expressed in the following way: s=singlet; d=doublet; t=triplet; bs=unresolved peak or broad single; H=proton (for the rotamers, H$_m$ and H$_m$ are denoted with reference to the major and minor isomers M and m respectively), in the LC/MS column, the following are successively indicated: the analytical high performance liquid chromatography method used (A. B or C) and detailed below, the retention time of the compound expressed in minutes, and the MH$^+$ peak identified by mass spectrometry.

Method A: HPLC/TOF

Column: Acquity BEH C18, 50×2.1 mm, 1.7 μm

Solvent A: H$_2$O+0.05% TFA; solvent B: ACN+0.035% TFA; flow rate=1 ml/min

Gradient 3 min: T0: 98% A—T1.6 to T2.1 min: 100% B—T2.5 to T 3 min: 98% A

T°=40° C.

Detection: 220 nm

Ionization: ESI+

Method B: HPLC/ZQ CH$_3$COONH$_4$ 5 mM/ACN

Column: Kromasil C18, 50×2.1 mm, 3.5 μm

Solvent A: CH$_3$COONH$_4$+3% ACN; solvent B: ACN; flow rate=0.8 ml/min

Gradient 10 min: T0: 100% A—T5.5 to T7 min: 100% B—T7.1 to T10 min: 100% A

T°=40° C.

Detection: 220 nm

Ionization: ESI+

TABLE

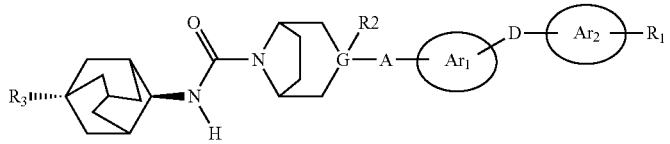

(I)

| No. | G | A* | D* | Ar1 | Ar2 | R1 | R2** | R3 | Mp | LC-MS | Route |
|---|---|---|---|---|---|---|---|---|---|---|---|
| 1 | C | — | — | A-phenyl-D | D-piperazine-N-R1 | —SO2—Me | H | OH | 250 | A 1.79 543 | A |
| 2 | C | — | O | A-phenyl-D | D-pyridine | H | H | OH | 103 | A 1.80 474 | A |
| 3 | C | — | — | A-phenyl-D | D-piperazine-N-R1 | —SO2—Me | OH endo | OH | >250 | B 3.15 559 | B |
| 4 | C | — | — | A-phenyl-D | D-piperazine-N-R1 | —SO2—Me | OH endo | —C(O)NH2 | 276 | B 3.1 586 | B |
| 5 | C | O | — | A-phenyl-D | D-piperazine-N-R1 | —SO2—Me | H endo | OH | 146 | A 0.86 559 | Ca |
| 6 | C | O | — | A-phenyl-D | D-piperazine-N-R1 | —SO2—Me | H endo | —C(O)NH2 | 247 | A 0.83 586 | Ca |
| 7 | C | O | — | A-phenyl-D | D-piperazine-N-R1 | —SO2—Me | H exo | OH | 252 | A 0.89 559 | Ca |
| 8 | C | O | — | A-phenyl-D | D-morpholine | H | H endo | —C(O)NH2 | 220 | A 0.74 509 | Ca |
| 9 | C | O | — | A-pyridine-D | D-phenyl-R1 | —OiPr | H endo | —C(O)NH2 | 255 | A 1.25 559 | Cb |
| 10 | C | O | — | A-pyridine-D | D-piperazine-N-R1 | —SO2—Me | H endo | —C(O)NH2 | 270 | B 3.33 587 | D |
| 11 | C | O | — | A-pyrimidine-D | D-phenyl-R1 | OMe | H endo | OH | 196 | A 1.09 505 | D |
| 12 | C | O | — | A-pyrimidine-D | D-phenyl-R1 | OMe | H endo | —C(O)NH2 | 238 | A 1.06 532 | D |
| 13 | C | —CH2—O— | — | A-phenyl-D | D-piperazine-N-R1 | —SO2—Me | H endo | OH | 225 | A 0.92 573 | Ca |

TABLE-continued (I)

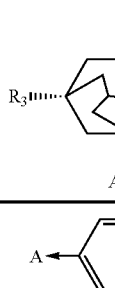

| No. | G | A* | D* | Ar1 | Ar2 | R1 | R2** | R3 | Mp | LC-MS | Route |
|---|---|---|---|---|---|---|---|---|---|---|---|
| 14 | C | —CH$_2$—O— | — | 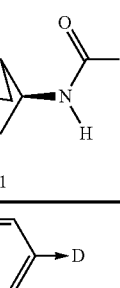 |  | —SO$_2$—Me | H endo | —C(O)NH$_2$ | 253 | A 0.9 600 | Ca |
| 15 | C | —CH$_2$—O— | — | 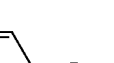 |  | —SO$_2$—Me | OH endo | OH | 249 | A 0.77 589 | E |
| 16 | C | —CH$_2$—O— | — |  | 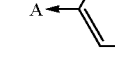 | —SO$_2$—Me | OH endo | —C(O)NH$_2$ | 210 | A 0.75 616 | E |
| 17 | C | —CH$_2$—O— | — | 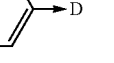 | 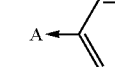 | —SO$_2$—Me | H exo | OH | 227 | A 0.91 573 | Ca |
| 18 | C | —CH$_2$—O— | — | 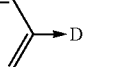 | 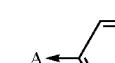 | —SO$_2$—Me | H exo | OH | 230 | A 0.85 574 | D |
| 19 | C | —CH$_2$—O— | — | 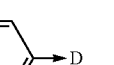 |  | —SO$_2$—Me | H exo | —C(O)NH$_2$ | 228 | A 0.82 601 | D |
| 20 | C | —CH$_2$—O— | — |  | 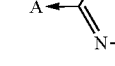 | -t-butyl | H exo | —C(O)NH$_2$ | 220 | A 0.73 579 | D |
| 21 | C | —CH$_2$—O— | — | 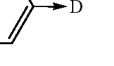 | 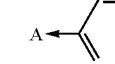 | -t-butyl | H exo | OH | 211 | A 0.74 552 | D |
| 22 | C | —CH$_2$—O— | — | 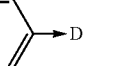 |  | —SO$_2$—Me | H endo | —C(O)NH$_2$ | 250 | A 0.84 601 | D |
| 23 | C | —CH$_2$—O— | — |  |  | -t-butyl | H endo | OH | 273 | A 0.75 552 | D |
| 24 | C | —CH$_2$—O— | — |  | 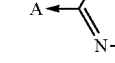 | -t-butyl | H endo | —C(O)NH$_2$ | 260 | A 0.74 579 | D |
| 25 | N | — | — | 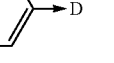 | 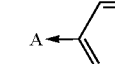 | —SO$_2$—Me | # | OH | 243 | A 0.66 545 | F |
| 26 | N | — | — | 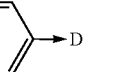 | | —SO$_2$—Me | # | —C(O)NH$_2$ | >250 | A 0.65 572 | F |

TABLE-continued

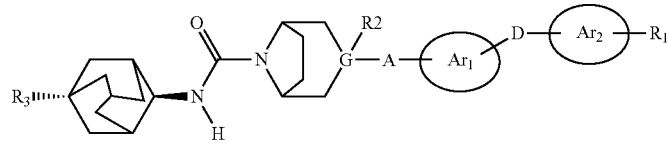
(I)

| No. | G | A* | D* | Ar1 | Ar2 | R1 | R2** | R3 | Mp | LC-MS | Route |
|---|---|---|---|---|---|---|---|---|---|---|---|
| 27 | C | O | — | A→ pyridine →D (N) | D→ phenyl →R1 | —Si(Me)₃ | H endo | —C(O)NH₂ | 276 | A 1.57 573 | Cb |

Route A corresponds to schemes 1 and 2
Route B corresponds to schemes 1, 3a and 4
Route Ca corresponds to schemes 1, 3a and 5
Route Cb corresponds to schemes 1, 3b and 5
Route D corresponds to schemes 1 and 7
Route E corresponds to schemes 1 and 8
Route F corresponds to schemes 1 and 6
In the table, the arrows indicate the positions of the bonds with the adjacent atom A or D
*the sign "—" signifies a bond
**the sign "#" signifies that R2 is absent The compounds according to the invention were the subject of pharmacological assays for determining their inhibitory effect on the 11beta-HSD1 enzyme which is an enzyme involved in lipid metabolism or glucose metabolism.

These assays consisted in measuring the in vitro inhibitory activity of the compounds of the invention by means of an SPA (Scintillation Proximity Assay) in 384-well format. Recombinant 11beta-HSD1 protein was produced in the yeast *S. cerevisiae*. The reaction was carried out by incubating the enzyme in the presence of $^3$H-cortisone and of NADPH, in the absence or presence of an increasing concentration of inhibitor. SPA beads coupled to an anti-mouse antibody, preincubated with an anti-cortisol antibody, made it possible to measure the amount of cortisol formed during the course of the reaction.

The inhibitory activity with respect to the 11beta-HSD1 enzyme is given by the concentration which inhibits 50% of the activity of 11beta-HSD1 ($IC_{50}$).

The $IC_{50}$ values of the compounds according to the invention are less than 1 µM. For example, the $IC_{50}$ values of compounds Nos. 5 and 17 are, respectively, 0.010 and 0.004 µM.

It therefore appears that the compounds according to the invention have an inhibitory activity on the 11beta-HSD1 enzyme. The compounds of the invention can therefore be used for the preparation of medicaments, in particular medicaments that inhibit the 11beta-HSD1 enzyme.

Thus, according to another of the aspects of the invention, a subject thereof is medicaments which comprise a compound of formula (I), or an addition salt of the latter with a pharmaceutically acceptable acid, or else a solvate of the compound of formula (I).

These medicaments are of use in therapy, in particular in the treatment of obesity, diabetes, insulin resistance, metabolic syndrome. Cushing's syndrome, hypertension, atherosclerosis, cognition and dementia, glaucoma, osteoporosis and certain infectious diseases by increasing the effectiveness of the immune system.

According to another of its aspects, the present invention relates to pharmaceutical compositions comprising a compound according to the invention as active ingredient. These pharmaceutical compositions contain an effective dose of at least one compound according to the invention or a pharmaceutically acceptable salt, a hydrate or a solvate of said compound, and also at least one pharmaceutically acceptable excipient.

Said excipients are chosen, according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or the optional salt, solvate or hydrate thereof, may be administered in unit administration form, as a mixture with conventional pharmaceutical excipients, to animals and to human beings for the prophylaxis or treatment of the conditions or diseases above.

Suitable unit administration forms comprise oral administration forms such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms, and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

According to another of its aspects, the present invention also relates to a method for treating the pathological conditions indicated above, which comprises administering an effective dose of a compound according to the invention, or a pharmaceutically acceptable salt or solvate thereof, to a patient.

The invention claimed is:

1. A compound corresponding to formula (I)

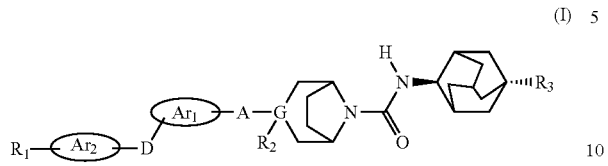

in which
- A is a bond or an —O—(CH$_2$)$_n$— group with n being a number equal to 0 or 1,
- D is a bond or an oxygen atom,
- G is a carbon or nitrogen atom,
- Ar1 is an aryl or heteroaryl group,
- Ar2 is an aryl or heteroaryl or heterocycloalkyl group,
- R1 is a hydrogen atom, or a (C1-C6)alkyl, —SO$_2$—(C1-C6)alkyl, —SO$_2$-halo(C1-C6)alkyl, (C1-C6)alkoxy or —Si(alkyl)$_3$ group,
- R2 is a hydrogen atom or a hydroxyl group or, when G is a nitrogen atom, R2 is absent,
- R3 is a hydroxyl or —C(O)-NH$_2$ group, in the form of a base or of an addition salt with an acid.

2. A compound of formula (I) as claimed in claim 1, wherein the substituents of the Ar1 group are in the para-position with respect to one another.

3. A compound of formula (I) as claimed in claim 1, wherein the substituents of the Ar2 group are in the para-position with respect to one another.

4. A compound of formula (I) as claimed in claim 1, wherein G is a carbon atom.

5. A compound of formula (I) as claimed in claim 1, wherein G is a nitrogen atom.

6. A compound of formula (I) as claimed in claim 1, wherein R3 is —C(O)—NH$_2$.

7. A process for preparing a compound of formula (I) as claimed in claim 1, wherein a compound of formula (IV):

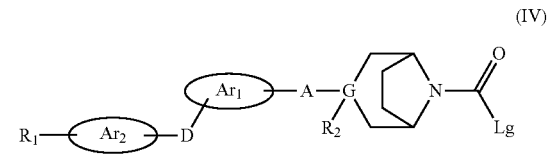

in which A, D, G, Ar1, Ar2, R1 and R2 are as defined in claim 1 and Lg is a leaving group, is reacted with a compound of formula (V):

in which R3 is as defined in claim 1, in the presence of a solvent and of a base.

8. A pharmaceutical composition, comprising the compound of formula (I) as claimed in claim 1 or a pharmaceutically acceptable salt, and at least one pharmaceutically acceptable excipient.

9. The A method of treating obesity, diabetes, insulin resistance, metabolic syndrome, Cushing's syndrome, hypertension, atherosclerosis, cognition and dementia, glaucoma, and osteoporosis by increasing the effectiveness of the immune system in a patient in need thereof comprising administering to said patient a therapeutically effecti ve amount of the pharmaceutical composition of claim 8.

* * * * *

UNITED STATES PATENT AND TRADEMARK OFFICE
CERTIFICATE OF CORRECTION

PATENT NO.         : 8,530,477 B2                                                    Page 1 of 1
APPLICATION NO. : 13/126195
DATED              : September 10, 2013
INVENTOR(S)        : Braun et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 228 days.

Signed and Sealed this

Fifteenth Day of September, 2015

Michelle K. Lee
*Director of the United States Patent and Trademark Office*